US008652839B2

(12) United States Patent
Kwee et al.

(10) Patent No.: US 8,652,839 B2
(45) Date of Patent: Feb. 18, 2014

(54) HM1.24—UTILIZING CANCER VACCINES

(75) Inventors: Yong Kwee, London (GB); Masaaki Kosaka, Tokushima (JP); Yasuo Koishihara, Chuo-ku (JP)

(73) Assignees: Chugai Seiyaku Kabushiki Kaisha, Tokyo (JP); University College London, London (GB)

( * ) Notice: Subject to any disclaimer, the term of this patent is extended or adjusted under 35 U.S.C. 154(b) by 728 days.

(21) Appl. No.: 10/533,104

(22) PCT Filed: Oct. 30, 2003

(86) PCT No.: PCT/JP03/13954
§ 371 (c)(1),
(2), (4) Date: Apr. 28, 2005

(87) PCT Pub. No.: WO2004/039398
PCT Pub. Date: May 13, 2004

(65) Prior Publication Data
US 2006/0153883 A1    Jul. 13, 2006

(30) Foreign Application Priority Data

Oct. 30, 2002 (JP) ................................. 2002-316639

(51) Int. Cl.
C12N 5/00 (2006.01)
C12N 5/02 (2006.01)
A01N 63/00 (2006.01)
A01N 65/00 (2009.01)

(52) U.S. Cl.
USPC .................. 435/325; 424/93.1; 424/93.21

(58) Field of Classification Search
None
See application file for complete search history.

(56) References Cited

U.S. PATENT DOCUMENTS 7,252,996 B2 *  8/2007  Boccaccio et al. ............ 435/377

FOREIGN PATENT DOCUMENTS

EP          1 059 533 A1     12/2000
WO        WO 01/77362 A1    10/2001

OTHER PUBLICATIONS

Stevenson et al., Curr. Opin. Oncol., 2005, 17:573-577.*
Komenaka et al., Clinics in Dermatology, 2004, 22: 251-265.*
Evans et al., Q. J. Med 1999: 92: 299-307.*
Chiriva-Internati et al., Cancer Gene Therapy, 2001, Dec., 8(Suppl 2): S27.*

Chiriva-Internati, Maurizio et al., "Sperm protein 17 (Sp17) is a suitable target for immunotherapy of multiple myeloma", Blood, vol. 100, No. 3, pp. 961-965, Aug. 1, 2002.
Thurner, Beatrice et al., "Vaccination with Mage-3A1 Peptide-pulsed Mature, Monocyte-derived Dendritic Cells Expands Specific Cytotoxic T Cells and Induces Regression of Some Metastases in Advanced Stage IV Melanoma", J. Exp. Med., vol. 190, No. 11, pp. 1669-1678, 1999.
Song, Wenru et al., "Dendritic Cells Genetically Modified with an Adenovirus Vector Encoding the cDNA for a Model Antigen Induce Protective and Therapeutic Antitumor Immunity", J. Exp. Med., vol. 186, No. 8, pp. 1247-1256, 1997.
Specht, Jennifer M. et al., "Dendritic Cells Retrovirally Transduced with a Model Antigen Gene are Therapeutically Effective against Established Pulmonary Metastases", J. Exp. Med., vol. 186, No. 8, pp. 1213-1221, 1997.
Treon, Steven P., et al., "Immunotherapeutic Strategies for the Treatment of Plasma Cell Malignancies", Seminars in Oncology, vol. 27, No. 5, pp. 598-613, 2000.
Condon, Cal et al, "DNA-based immunization by in vivo transfection of dendritic cells", Nature Medicine, vol. 2, No. 10, pp. 1122-1128, Oct. 1996.
Porgador, Angel et al., "Bone Marrow-generated Dendritic Cells Pulsed with a Class I-restricted Peptide Are Potent Inducers of Cytotoxic T Lymphocytes", J. Exp. Med., vol. 182, No. 1, pp. 255-260, Jul. 1995.
Gong, Jianlin et al., "Induction of antitumor activity by immunization with fusions of dendritic and carcinoma cells", Nature Medicine, vol. 3, No. 5, pp. 558-561, May 1997.
Szabolcs, Paul et al., "Retrovirally Transduced Human Dendritic Cells Express a Normal Phenotype and Potent T-Cell Stimulatory Capacity", Blood, vol. 90, No. 6, pp. 2160-2167, Sep. 1997.
Syrengelas, Anthanasia D. et al., "DNA immunization induces protective immunity against B-cell lymphoma", Nature Medicine, vol. 2, No. 9, pp. 1038-1041, Sep. 1996.
Hundemer et al., "Identification of T Cell Epitopes within the Plasmacell Antigen HM1.24", 2002, Blood, vol. 100, No. 11, p. Abstract No. 5088, XP009063835.
Nicola Di et al., "Gene Transfer into human dendritic antigen-presenting cells by vaccinia virus and adenovirus vectors", 1998, Cancer Gene Therapy, vol. 5, No. 6, pp. 350-356.
Ohtomo et al., "Molecular Cloning and Characterization of a Surface Antigen Preferentially Overexpressed on Multiple Myeloma Cells", Biochemical and Biophysical Research Communications, 1999, vol. 258, No. 3, pp. 583-591.
Ozaki et al., "Humanized Anti-HM1.24 Antibody Mediates Myeloma Cell Cytotoxicity That is Enhanced Cytokine Stimulation of Effector Cells", Blood, 1999, vol. 93, No. 11, pp. 3922-3930.
Rew, et al, "Potent anti-tumour cytotoxic T lymphocytes directed against the myloma antigen HM1.24", Blood, 2003, vol. 102, No. 11, p. 112A, XP009063769.

* cited by examiner

Primary Examiner — Hong Sang
(74) Attorney, Agent, or Firm — Foley & Lardner LLP

(57) ABSTRACT

A cancer vaccine containing as an active ingredient an antigen-specific dendritic cell pulsed by an HM1.24 protein, HM1.24 peptide or transduced with an HM1.24-encoding gene, or HM1.24 protein-encoding DNA or RNA.

8 Claims, 14 Drawing Sheets

Fig.4
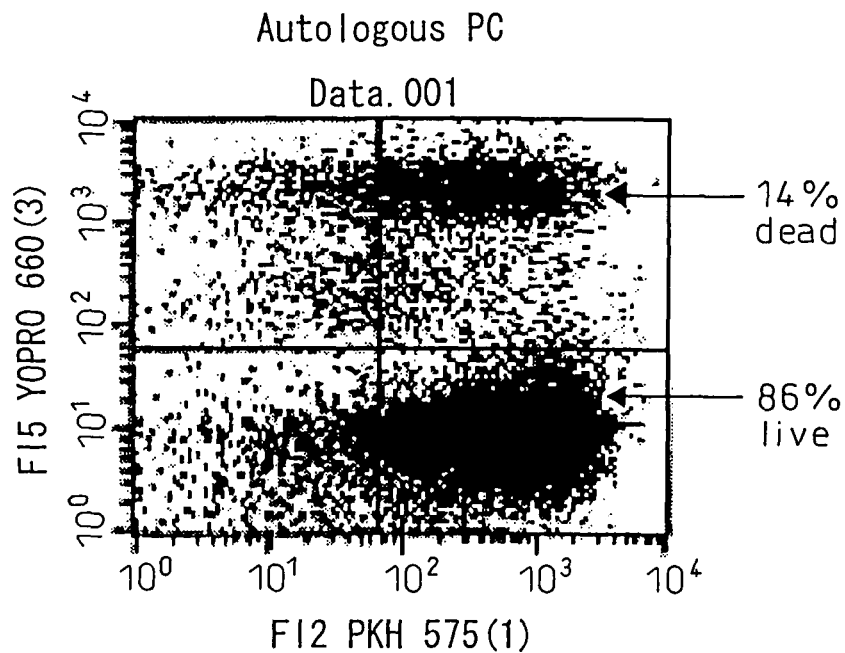
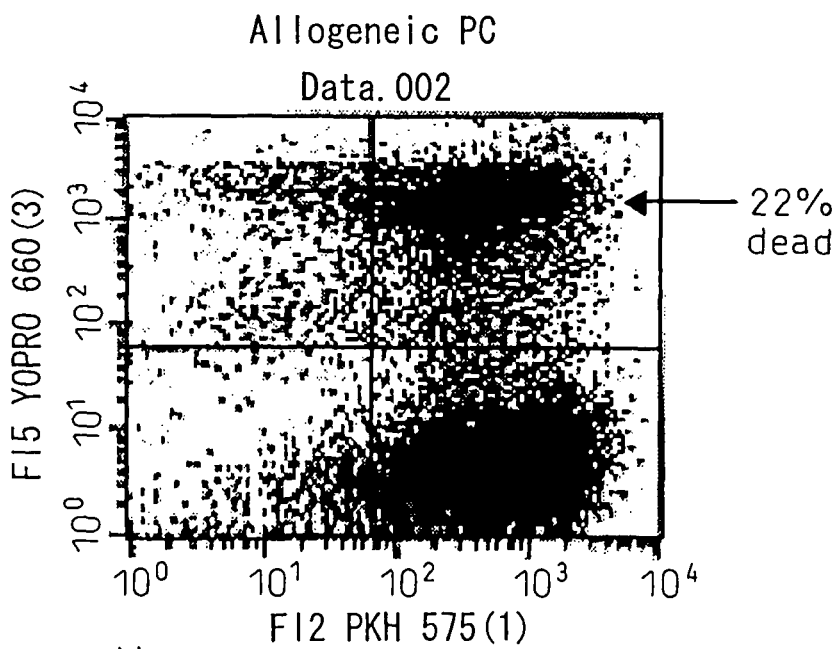
PC=plasma cells

Fig.6
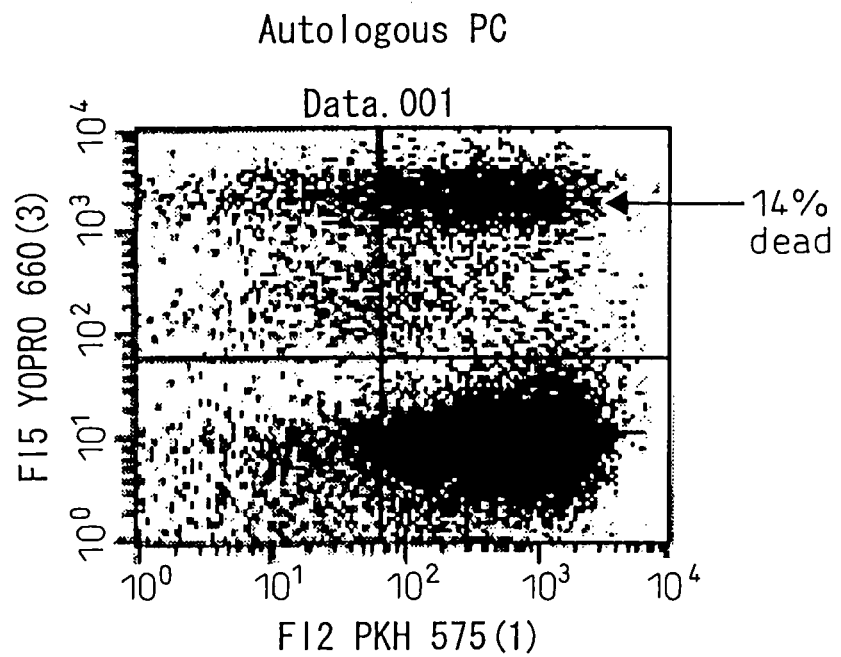
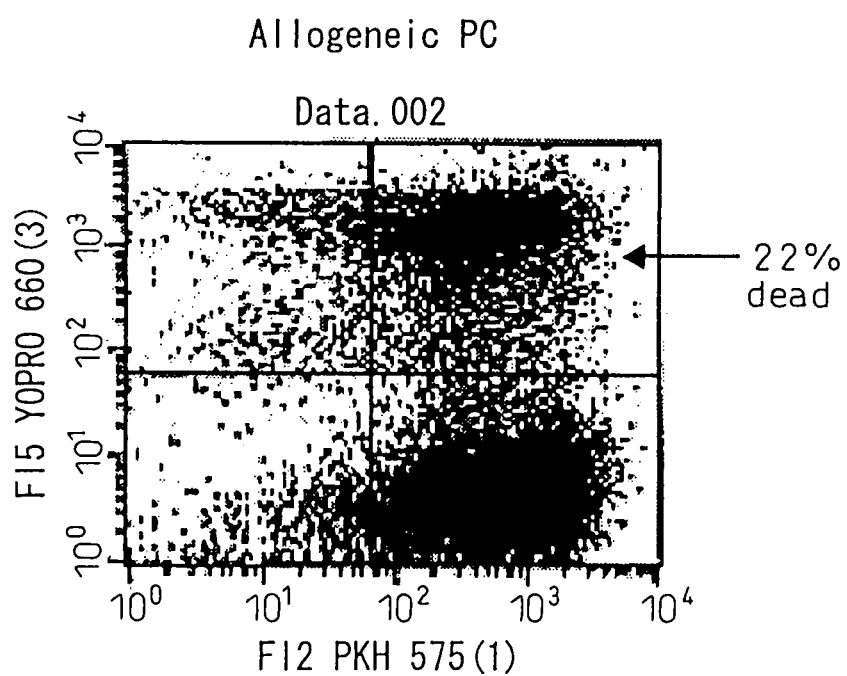

Fig.7
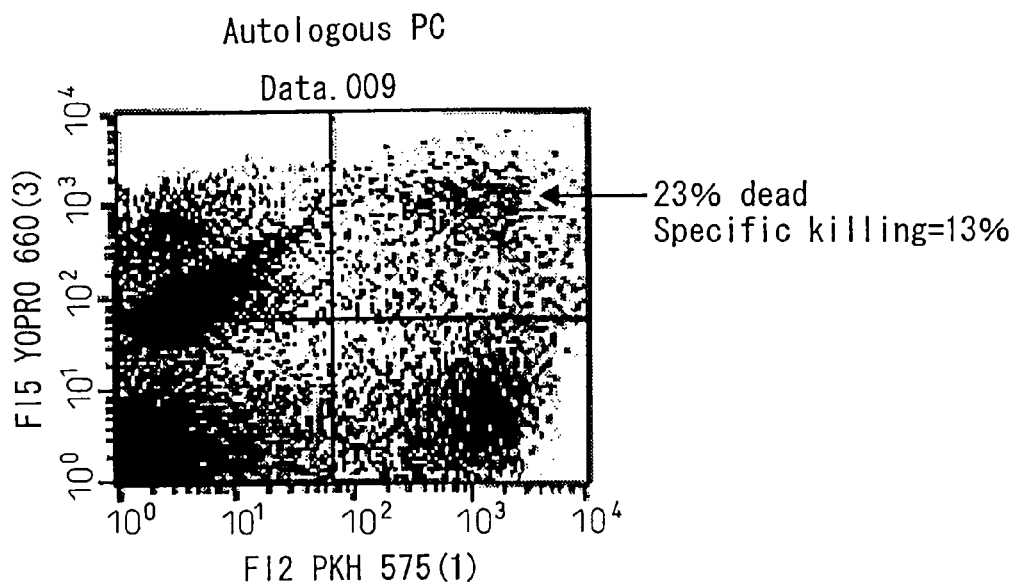
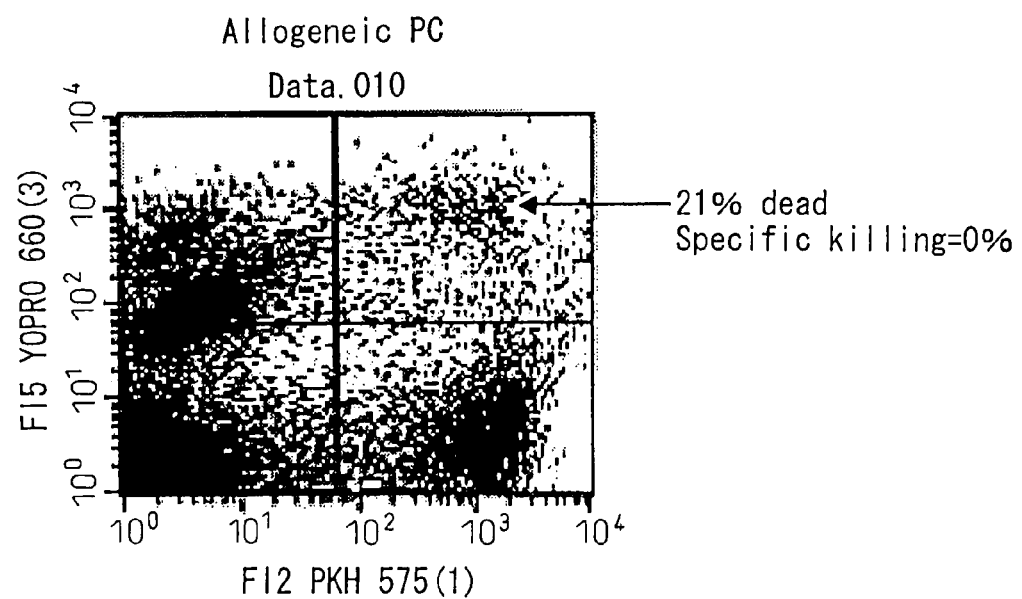

Fig.8
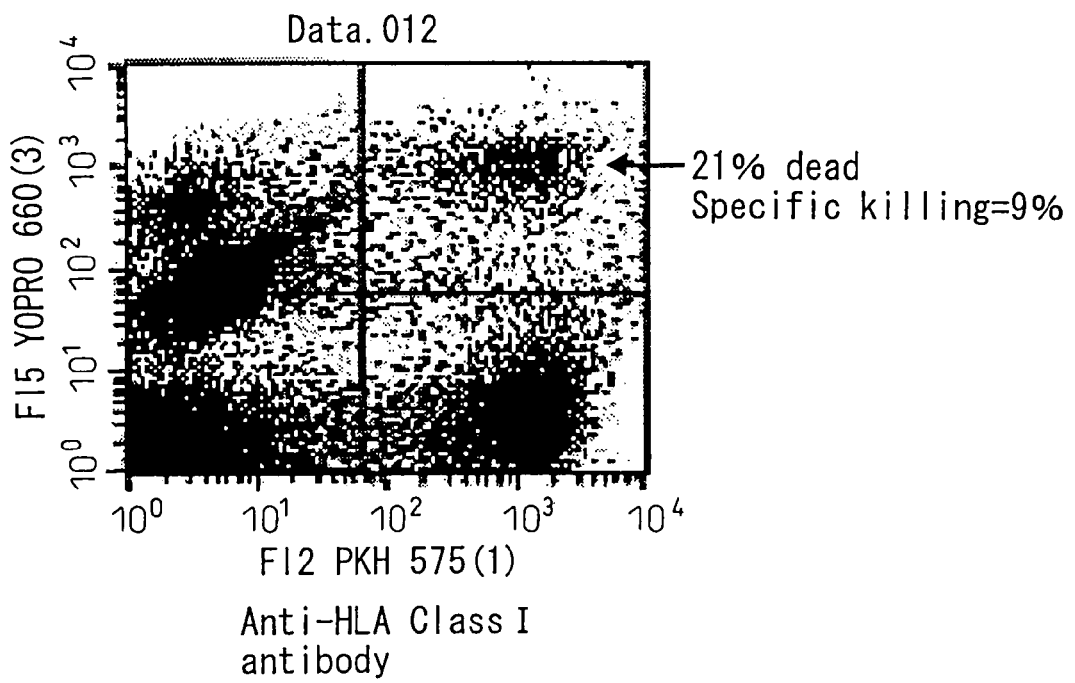
Anti-HLA Class I antibody
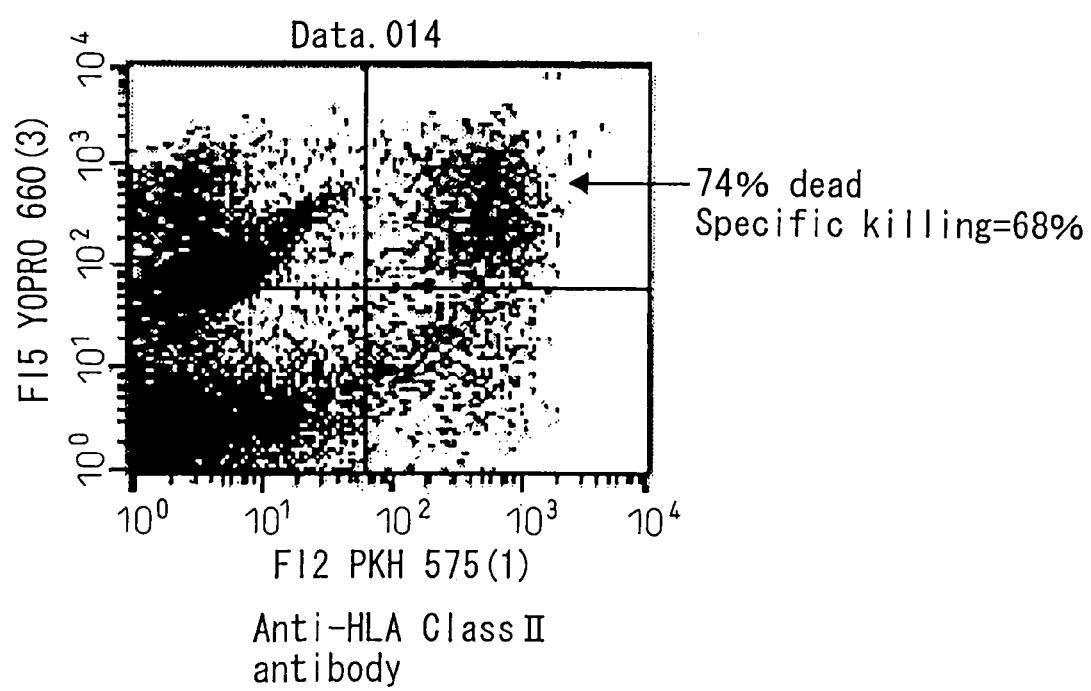
Anti-HLA Class II antibody

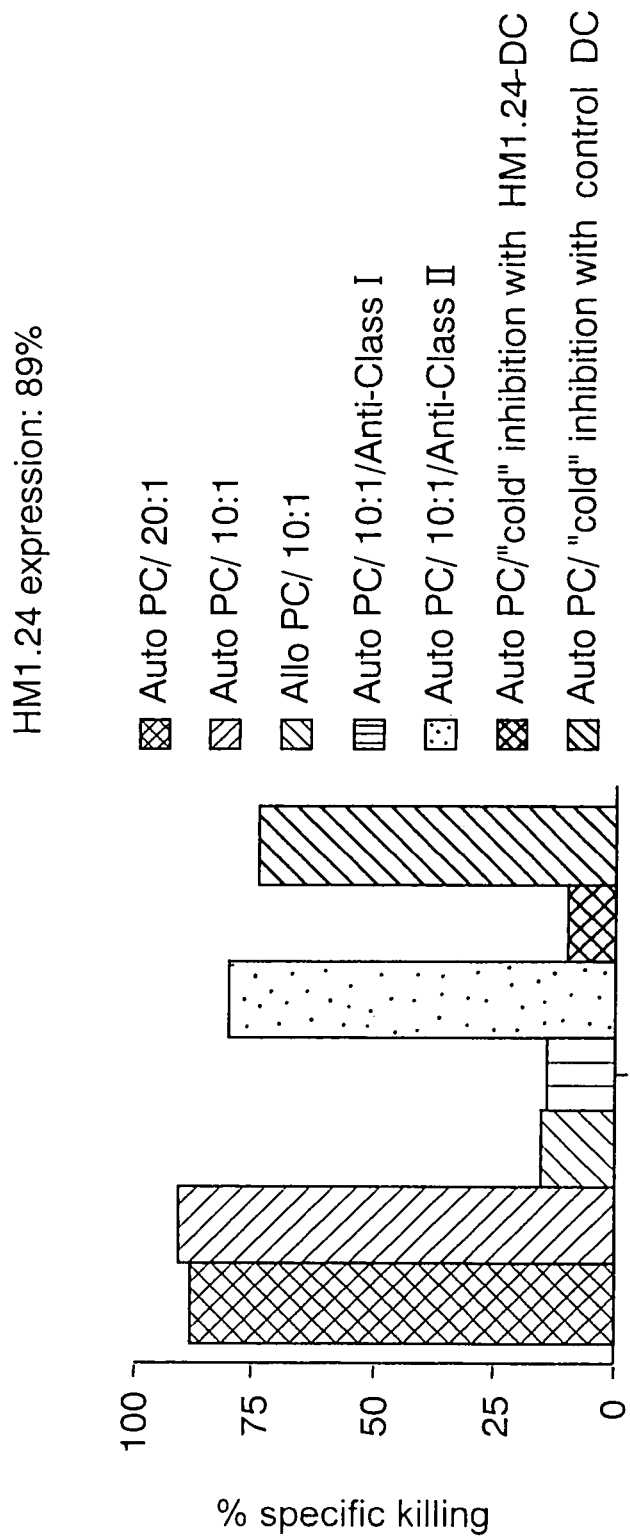

SEQUENCE LISTING

```
<160> NUMBER OF SEQ ID NOS: 23

<210> SEQ ID NO 1
<211> LENGTH: 109
<212> TYPE: DNA
<213> ORGANISM: Artificial Sequence
<220> FEATURE:
<223> OTHER INFORMATION: Description of Artificial Sequence: Synthetic
      DNA comprising leader sequence and HA coding sequence

<400> SEQUENCE: 1
aattcccacc atgggatgga gctgtatcat cctcttcttg gtagcaacag ctacaggtgt      60
ccactcatac ccatacgacg tcccagacta cgctggtacc gcggccgcg                 109

<210> SEQ ID NO 2
<211> LENGTH: 109
<212> TYPE: DNA
<213> ORGANISM: Artificial Sequence
<220> FEATURE:
<223> OTHER INFORMATION: Description of Artificial Sequence: Synthetic
      DNA comprising leader sequence and HA coding sequence

<400> SEQUENCE: 2
gatccgcggc cgcggtacca gcgtagtctg ggacgtcgta tgggtatgag tggacacctg      60
tagctgttgc taccaagaag aggatgatac agctccatcc catggtggg                 109

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taaaggtacc aacagcgagg cctgccg                                          27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgctgcagt gagatcccag gatccata                                         28

<210> SEQ ID NO 5
<211> LENGTH: 396
<212> TYPE: DNA
<213> ORGANISM: Homo sapiens
<220> FEATURE:
<221> NAME/KEY: CDS
<222> LOCATION: (1)..(396)
```

-continued

```
<220> FEATURE:
<223> OTHER INFORMATION: Nucleotide sequence of extracellular domain of
      soluble HM 1.24 antigenic protein

<400> SEQUENCE: 5 aac agc gag gcc tgc cgg gac ggc ctt cgg gca gtg atg gag tgt cgc        48
Asn Ser Glu Ala Cys Arg Asp Gly Leu Arg Ala Val Met Glu Cys Arg
 1               5                  10                  15 aat gtc acc cat ctc ctg caa caa gag ctg acc gag gcc cag aag ggc        96
Asn Val Thr His Leu Leu Gln Gln Glu Leu Thr Glu Ala Gln Lys Gly
            20                  25                  30 ttt cag gat gtg gag gcc cag gcc gcc acc tgc aac cac act gtg atg       144
Phe Gln Asp Val Glu Ala Gln Ala Ala Thr Cys Asn His Thr Val Met
        35                  40                  45 gcc cta atg gct tcc ctg gat gca gag aag gcc caa gga caa aag aaa       192
Ala Leu Met Ala Ser Leu Asp Ala Glu Lys Ala Gln Gly Gln Lys Lys
    50                  55                  60 gtg gag gag ctt gag gga gag atc act aca tta aac cat aag ctt cag       240
Val Glu Glu Leu Glu Gly Glu Ile Thr Thr Leu Asn His Lys Leu Gln
65                  70                  75                  80 gac gcg tct gca gag gtg gag cga ctg aga aga gaa aac cag gtc tta       288
Asp Ala Ser Ala Glu Val Glu Arg Leu Arg Arg Glu Asn Gln Val Leu
                85                  90                  95 agc gtg aga atc gcg gac aag aag tac tac ccc agc tcc cag gac tcc       336
Ser Val Arg Ile Ala Asp Lys Lys Tyr Tyr Pro Ser Ser Gln Asp Ser
            100                 105                 110 agc tcc gct gcg gcg ccc cag ctg ctg att gtg ctg ctg ggc ctc agc       384
Ser Ser Ala Ala Ala Pro Gln Leu Leu Ile Val Leu Leu Gly Leu Ser
        115                 120                 125 gct ctg ctg cag                                                       396
Ala Leu Leu Gln
    130

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ataggatcct caagcggagc tggagtcctg                                       30

<210> SEQ ID NO 7
<211> LENGTH: 345
<212> TYPE: DNA
<213> ORGANISM: Homo sapiens
<220> FEATURE:
<221> NAME/KEY: CDS
<222> LOCATION: (1)..(345)
<220> FEATURE:
<223> OTHER INFORMATION: Nucleotide sequence of extracellular domain of
      C-terminal lacking soluble HM 1.24 antigenic
      protein

<400> SEQUENCE: 7 aac agc gag gcc tgc cgg gac ggc ctt cgg gca gtg atg gag tgt cgc        48
Asn Ser Glu Ala Cys Arg Asp Gly Leu Arg Ala Val Met Glu Cys Arg
 1               5                  10                  15 aat gtc acc cat ctc ctg caa caa gag ctg acc gag gcc cag aag ggc        96
Asn Val Thr His Leu Leu Gln Gln Glu Leu Thr Glu Ala Gln Lys Gly
            20                  25                  30 ttt cag gat gtg gag gcc cag gcc gcc acc tgc aac cac act gtg atg       144
Phe Gln Asp Val Glu Ala Gln Ala Ala Thr Cys Asn His Thr Val Met
```

```
                  35                  40                  45
gcc cta atg gct tcc ctg gat gca gag aag gcc caa gga caa aag aaa    192
Ala Leu Met Ala Ser Leu Asp Ala Glu Lys Ala Gln Gly Gln Lys Lys
     50                  55                  60 gtg gag gag ctt gag gga gag atc act aca tta aac cat aag ctt cag    240
Val Glu Glu Leu Glu Gly Glu Ile Thr Thr Leu Asn His Lys Leu Gln
 65                  70                  75                  80 gac gcg tct gca gag gtg gag cga ctg aga aga gaa aac cag gtc tta    288
Asp Ala Ser Ala Glu Val Glu Arg Leu Arg Arg Glu Asn Gln Val Leu
                 85                  90                  95 agc gtg aga atc gcg gac aag aag tac tac ccc agc tcc cag gac tcc    336
Ser Val Arg Ile Ala Asp Lys Lys Tyr Tyr Pro Ser Ser Gln Asp Ser
            100                 105                 110 agc tcc gct                                                        345
Ser Ser Ala
        115

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatcttggt tcattctcaa gcctcagaca gt                                32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctcagactc ggcctgaccc gtggaaagaa                                   30

<210> SEQ ID NO 10
<211> LENGTH: 429
<212> TYPE: DNA
<213> ORGANISM: Artificial Sequence
<220> FEATURE:
<223> OTHER INFORMATION: Description of Artificial Sequence: Synthetic
      nucleotide sequence coding for a fusion protein
      comprising HA peptide and soluble HM 1.24
      antigenic protein
<220> FEATURE:
<221> NAME/KEY: CDS
<222> LOCATION: (1)..(429)

<400> SEQUENCE: 10 tac cca tac gac gtc cca gac tac gct ggt acc aac agc gag gcc tgc    48
Tyr Pro Tyr Asp Val Pro Asp Tyr Ala Gly Thr Asn Ser Glu Ala Cys
  1               5                  10                  15 cgg gac ggc ctt cgg gca gtg atg gag tgt cgc aat gtc acc cat ctc    96
Arg Asp Gly Leu Arg Ala Val Met Glu Cys Arg Asn Val Thr His Leu
                 20                  25                  30 ctg caa caa gag ctg acc gag gcc cag aag ggc ttt cag gat gtg gag   144
Leu Gln Gln Glu Leu Thr Glu Ala Gln Lys Gly Phe Gln Asp Val Glu
             35                  40                  45 gcc cag gcc gcc acc tgc aac cac act gtg atg gcc cta atg gct tcc   192
Ala Gln Ala Ala Thr Cys Asn His Thr Val Met Ala Leu Met Ala Ser
 50                  55                  60
```

```
ctg gat gca gag aag gcc caa gga caa aag aaa gtg gag gag ctt gag       240
Leu Asp Ala Glu Lys Ala Gln Gly Gln Lys Lys Val Glu Glu Leu Glu
 65                  70                  75                  80 gga gag atc act aca tta aac cat aag ctt cag gac gcg tct gca gag       288
Gly Glu Ile Thr Thr Leu Asn His Lys Leu Gln Asp Ala Ser Ala Glu
                 85                  90                  95 gtg gag cga ctg aga aga gaa aac cag gtc tta agc gtg aga atc gcg       336
Val Glu Arg Leu Arg Arg Glu Asn Gln Val Leu Ser Val Arg Ile Ala
            100                 105                 110 gac aag aag tac tac ccc agc tcc cag gac tcc agc tcc gct gcg gcg       384
Asp Lys Lys Tyr Tyr Pro Ser Ser Gln Asp Ser Ser Ser Ala Ala Ala
        115                 120                 125 ccc cag ctg ctg att gtg ctg ctg ggc ctc agc gct ctg ctg cag           429
Pro Gln Leu Leu Ile Val Leu Leu Gly Leu Ser Ala Leu Leu Gln
    130                 135                 140

<210> SEQ ID NO 11
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleotide sequence coding for a fusion protein
      comprising HA peptide and C-terminal lacking
      soluble HM 1.24 antigenic protein
<220> FEATURE:
<221> NAME/KEY: CDS
<222> LOCATION: (1)..(378)

<400> SEQUENCE: 11 tac cca tac gac gtc cca gac tac gct ggt acc aac agc gag gcc tgc       48
Tyr Pro Tyr Asp Val Pro Asp Tyr Ala Gly Thr Asn Ser Glu Ala Cys
  1               5                  10                  15 cgg gac ggc ctt cgg gca gtg atg gag tgt cgc aat gtc acc cat ctc       96
Arg Asp Gly Leu Arg Ala Val Met Glu Cys Arg Asn Val Thr His Leu
             20                  25                  30 ctg caa caa gag ctg acc gag gcc cag aag ggc ttt cag gat gtg gag       144
Leu Gln Gln Glu Leu Thr Glu Ala Gln Lys Gly Phe Gln Asp Val Glu
         35                  40                  45 gcc cag gcc gcc acc tgc aac cac act gtg atg gcc cta atg gct tcc       192
Ala Gln Ala Ala Thr Cys Asn His Thr Val Met Ala Leu Met Ala Ser
     50                  55                  60 ctg gat gca gag aag gcc caa gga caa aag aaa gtg gag gag ctt gag       240
Leu Asp Ala Glu Lys Ala Gln Gly Gln Lys Lys Val Glu Glu Leu Glu
 65                  70                  75                  80 gga gag atc act aca tta aac cat aag ctt cag gac gcg tct gca gag       288
Gly Glu Ile Thr Thr Leu Asn His Lys Leu Gln Asp Ala Ser Ala Glu
                 85                  90                  95 gtg gag cga ctg aga aga gaa aac cag gtc tta agc gtg aga atc gcg       336
Val Glu Arg Leu Arg Arg Glu Asn Gln Val Leu Ser Val Arg Ile Ala
            100                 105                 110 gac aag aag tac tac ccc agc tcc cag gac tcc agc tcc gct                378
Asp Lys Lys Tyr Tyr Pro Ser Ser Gln Asp Ser Ser Ser Ala
        115                 120                 125

<210> SEQ ID NO 12
<211> LENGTH: 379
<212> TYPE: DNA
<213> ORGANISM: Artificial Sequence
<220> FEATURE:
<223> OTHER INFORMATION: Description of Artificial Sequence: Synthetic
      nucleotide sequence coding for L chain V region
      version a of humanized anti-HM 1.24 antibody
<220> FEATURE:
<221> NAME/KEY: CDS
<222> LOCATION: (1)..(378)
```

<220> FEATURE:
<221> NAME/KEY: sig_peptide
<222> LOCATION: (1)..(57)
<220> FEATURE:
<221> NAME/KEY: mat_peptide
<222> LOCATION: (58)..(378)

<400> SEQUENCE: 12

```
atg gga tgg agc tgt atc atc ctc tcc ttg gta gca aca gct aca ggt      48
Met Gly Trp Ser Cys Ile Ile Leu Ser Leu Val Ala Thr Ala Thr Gly
            -15                 -10                  -5 gtc cac tcc gac atc cag atg acc cag agc cca agc agc ctg agc gcc      96
Val His Ser Asp Ile Gln Met Thr Gln Ser Pro Ser Ser Leu Ser Ala
        -1   1               5                  10 agc gtg ggt gac aga gtg acc atc acc tgt aag gct agt cag gat gtg     144
Ser Val Gly Asp Arg Val Thr Ile Thr Cys Lys Ala Ser Gln Asp Val
 15                  20                  25 aat act gct gta gcc tgg tac cag cag aag cca gga aag gct cca aag     192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga     240
Leu Leu Ile Tyr Ser Ala Ser Asn Arg Tyr Thr Gly Val Pro Ser Arg
             50                  55                  60 ttc agc ggt agc ggt agc ggt acc gac ttc acc ttc acc atc agc agc     288
Phe Ser Gly Ser Gly Ser Gly Thr Asp Phe Thr Phe Thr Ile Ser Ser
             65                  70                  75 ctc cag cca gag gac atc gct acc tac tac tgc cag caa cat tat agt     336
Leu Gln Pro Glu Asp Ile Ala Thr Tyr Tyr Cys Gln Gln His Tyr Ser
         80                  85                  90 act cca ttc acg ttc ggc caa ggg acc aag gtg gaa atc aaa c           379
Thr Pro Phe Thr Phe Gly Gln Gly Thr Lys Val Glu Ile Lys
     95                 100                 105
```

<210> SEQ ID NO 13
<211> LENGTH: 418
<212> TYPE: DNA
<213> ORGANISM: Artificial Sequence
<220> FEATURE:
<223> OTHER INFORMATION: Description of Artificial Sequence: Synthetic
      nucleotide sequence coding for H chain V region
      version r of humanized anti-HM 1.24 antibody
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 13

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
```

```
                50                      55                      60
cag aag ttc aag ggc aga gtc acc atg acc gca gac aag tcc acg agc     288
Gln Lys Phe Lys Gly Arg Val Thr Met Thr Ala Asp Lys Ser Thr Ser
                65                      70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
            80                      85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
        95                     100                 105 tgg ggg caa ggg acc acg gtc acc gtc tcc tca g                       418
Trp Gly Gln Gly Thr Thr Val Thr Val Ser Ser
110                 115                 120

<210> SEQ ID NO 14
<211> LENGTH: 418
<212> TYPE: DNA
<213> ORGANISM: Artificial Sequence
<220> FEATURE:
<223> OTHER INFORMATION: Description of Artificial Sequence: Synthetic
      nucleotide sequence coding for H chain V region
      version s of humanized anti-HM 1.24 antibody
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 14 atg gac tgg acc tgg agg gtc ttc ttc ttg ctg gct gta gct cca ggt     48
Met Asp Trp Thr Trp Arg Val Phe Phe Leu Leu Ala Val Ala Pro Gly
                -15                 -10                 -5 gct cac tcc cag gtg cag ctg gtg cag tct ggg gct gag gtg aag aag     96
Ala His Ser Gln Val Gln Leu Val Gln Ser Gly Ala Glu Val Lys Lys
        -1  1                   5                  10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
    15                      20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
30                      35                  40                  45 gag tgg atg gga tct att ttt cct gga gat ggt gat act agg tac agt    240
Glu Trp Met Gly Ser Ile Phe Pro Gly Asp Gly Asp Thr Arg Tyr Ser
                50                      55                  60 cag aag ttc aag ggc aga gtc acc atc acc gca gac aag tcc acg agc    288
Gln Lys Phe Lys Gly Arg Val Thr Ile Thr Ala Asp Lys Ser Thr Ser
                65                      70                  75 aca gcc tac atg gag ctg agc agc ctg aga tct gag gac acg gcc gtg    336
Thr Ala Tyr Met Glu Leu Ser Ser Leu Arg Ser Glu Asp Thr Ala Val
            80                      85                  90 tat tac tgt gcg aga gga tta cga cga ggg ggg tac tac ttt gac tac    384
Tyr Tyr Cys Ala Arg Gly Leu Arg Arg Gly Gly Tyr Tyr Phe Asp Tyr
        95                     100                 105 tgg ggg caa ggg acc acg gtc acc gtc tcc tca g                      418
Trp Gly Gln Gly Thr Thr Val Thr Val Ser Ser
110                 115                 120

<210> SEQ ID NO 15
<211> LENGTH: 1014
<212> TYPE: DNA
<213> ORGANISM: Homo sapiens
```

<220> FEATURE:
<223> OTHER INFORMATION: Nucleotide sequence coding for human HM 1.24
    antigenic protein expressed on cell membrane
<220> FEATURE:
<221> NAME/KEY: CDS
<222> LOCATION: (23)..(562)

<400> SEQUENCE: 15

| | | |
|---|---|---|
| gaattcggca cgagggatct gg atg gca tct act tcg tat gac tat tgc aga | | 52 |
| Met Ala Ser Thr Ser Tyr Asp Tyr Cys Arg | | |
| 1               5                   10 | | |
| gtg ccc atg gaa gac ggg gat aag cgc tgt aag ctt ctg ctg ggg ata | | 100 |
| Val Pro Met Glu Asp Gly Asp Lys Arg Cys Lys Leu Leu Leu Gly Ile | | |
|         15                  20                  25 | | |
| gga att ctg gtg ctc ctg atc atc gtg att ctg ggg gtg ccc ttg att | | 148 |
| Gly Ile Leu Val Leu Leu Ile Ile Val Ile Leu Gly Val Pro Leu Ile | | |
|     30                  35                  40 | | |
| atc ttc acc atc aag gcc aac agc gag gcc tgc cgg gac ggc ctt cgg | | 196 |
| Ile Phe Thr Ile Lys Ala Asn Ser Glu Ala Cys Arg Asp Gly Leu Arg | | |
|             45                  50                  55 | | |
| gca gtg atg gag tgt cgc aat gtc acc cat ctc ctg caa caa gag ctg | | 244 |
| Ala Val Met Glu Cys Arg Asn Val Thr His Leu Leu Gln Gln Glu Leu | | |
| 60                  65                  70 | | |
| acc gag gcc cag aag ggc ttt cag gat gtg gag gcc cag gcc gcc acc | | 292 |
| Thr Glu Ala Gln Lys Gly Phe Gln Asp Val Glu Ala Gln Ala Ala Thr | | |
| 75                  80                  85                  90 | | |
| tgc aac cac act gtg atg gcc cta atg gct tcc ctg gat gca gag aag | | 340 |
| Cys Asn His Thr Val Met Ala Leu Met Ala Ser Leu Asp Ala Glu Lys | | |
|         95                  100                 105 | | |
| gcc caa gga caa aag aaa gtg gag gag ctt gag gga gag atc act aca | | 388 |
| Ala Gln Gly Gln Lys Lys Val Glu Glu Leu Glu Gly Glu Ile Thr Thr | | |
|     110                 115                 120 | | |
| tta aac cat aag ctt cag gac gcg tct gca gag gtg gag cga ctg aga | | 436 |
| Leu Asn His Lys Leu Gln Asp Ala Ser Ala Glu Val Glu Arg Leu Arg | | |
|             125                 130                 135 | | |
| aga gaa aac cag gtc tta agc gtg aga atc gcg gac aag aag tac tac | | 484 |
| Arg Glu Asn Gln Val Leu Ser Val Arg Ile Ala Asp Lys Lys Tyr Tyr | | |
| 140                 145                 150 | | |
| ccc agc tcc cag gac tcc agc tcc gct gcg gcg ccc cag ctg ctg att | | 532 |
| Pro Ser Ser Gln Asp Ser Ser Ser Ala Ala Ala Pro Gln Leu Leu Ile | | |
| 155                 160                 165                 170 | | |
| gtg ctg ctg ggc ctc agc gct ctg ctg cag tgagatccca ggaagctggc | | 582 |
| Val Leu Leu Gly Leu Ser Ala Leu Leu Gln | | |
|         175                 180 | | |
| acatcttgga aggtccgtcc tgctcggctt ttcgcttgaa cattcccttg atctcatcag | | 642 |
| ttctgagcgg gtcatggggc aacacggtta gcggggagag cacggggtag ccggagaagg | | 702 |
| gcctctggag caggtctgga ggggccatgg ggcagtcctg ggtgtgggga cacagtcggg | | 762 |
| ttgacccagg gctgtctccc tccagagcct ccctccggac aatgagtccc ccctcttgtc | | 822 |
| tcccaccctg agattgggca tggggtgcgg tgtgggggc atgtgctgcc tgttgttatg | | 882 |
| ggttttttt gcggggggggg ttgctttttt ctggggtctt tgagctccaa aaaaataaac | | 942 |
| acttcctttg agggagagca caccttaaaa aaaaaaaaaa aaaaaaaaaa aaaaaattc | | 1002 |
| gggcggccgc ca | | 1014 |

<210> SEQ ID NO 16
<211> LENGTH: 132
<212> TYPE: PRT
<213> ORGANISM: Homo sapiens
<220> FEATURE:
<223> OTHER INFORMATION: Amino acid sequence of soluble HM 1.24

-continued

```
      antigenic protein

<400> SEQUENCE: 16

Asn Ser Glu Ala Cys Arg Asp Gly Leu Arg Ala Val Met Glu Cys Arg
  1               5                  10                  15

Asn Val Thr His Leu Leu Gln Gln Glu Leu Thr Glu Ala Gln Lys Gly
             20                  25                  30

Phe Gln Asp Val Glu Ala Gln Ala Ala Thr Cys Asn His Thr Val Met
         35                  40                  45

Ala Leu Met Ala Ser Leu Asp Ala Glu Lys Ala Gln Gly Gln Lys Lys
     50                  55                  60

Val Glu Glu Leu Glu Gly Glu Ile Thr Thr Leu Asn His Lys Leu Gln
 65                  70                  75                  80

Asp Ala Ser Ala Glu Val Glu Arg Leu Arg Arg Glu Asn Gln Val Leu
                 85                  90                  95

Ser Val Arg Ile Ala Asp Lys Lys Tyr Tyr Pro Ser Ser Gln Asp Ser
            100                 105                 110

Ser Ser Ala Ala Ala Pro Gln Leu Leu Ile Val Leu Leu Gly Leu Ser
        115                 120                 125

Ala Leu Leu Gln
        130

<210> SEQ ID NO 17
<211> LENGTH: 115
<212> TYPE: PRT
<213> ORGANISM: Homo sapiens
<220> FEATURE:
<223> OTHER INFORMATION: Amino acid sequence of extracellular downing
      of C-terminal lacking soluble HM 1.24 antigenic protein

<400> SEQUENCE: 17

Asn Ser Glu Ala Cys Arg Asp Gly Leu Arg Ala Val Met Glu Cys Arg
  1               5                  10                  15

Asn Val Thr His Leu Leu Gln Gln Glu Leu Thr Glu Ala Gln Lys Gly
             20                  25                  30

Phe Gln Asp Val Glu Ala Gln Ala Ala Thr Cys Asn His Thr Val Met
         35                  40                  45

Ala Leu Met Ala Ser Leu Asp Ala Glu Lys Ala Gln Gly Gln Lys Lys
     50                  55                  60

Val Glu Glu Leu Glu Gly Glu Ile Thr Thr Leu Asn His Lys Leu Gln
 65                  70                  75                  80

Asp Ala Ser Ala Glu Val Glu Arg Leu Arg Arg Glu Asn Gln Val Leu
                 85                  90                  95

Ser Val Arg Ile Ala Asp Lys Lys Tyr Tyr Pro Ser Ser Gln Asp Ser
            100                 105                 110

Ser Ser Ala
        115

<210> SEQ ID NO 18
<211> LENGTH: 143
<212> TYPE: PRT
<213> ORGANISM: Artificial Sequence
<220> FEATURE:
<223> OTHER INFORMATION: Description of Artificial Sequence: Synthetic
      amino acid sequence of a fusion protein
      comprising HA peptide and soluble HM 1.24
      antigenic protein

<400> SEQUENCE: 18

Tyr Pro Tyr Asp Val Pro Asp Tyr Ala Gly Thr Asn Ser Glu Ala Cys
```

```
              1               5                  10                 15
Arg Asp Gly Leu Arg Ala Val Met Glu Cys Arg Asn Val Thr His Leu
                    20                  25                 30

Leu Gln Gln Glu Leu Thr Glu Ala Gln Lys Gly Phe Gln Asp Val Glu
                35                  40                 45

Ala Gln Ala Ala Thr Cys Asn His Thr Val Met Ala Leu Met Ala Ser
        50                  55                 60

Leu Asp Ala Glu Lys Ala Gln Gly Gln Lys Lys Val Glu Glu Leu Glu
65                  70                  75                 80

Gly Glu Ile Thr Thr Leu Asn His Lys Leu Gln Asp Ala Ser Ala Glu
                85                  90                 95

Val Glu Arg Leu Arg Arg Glu Asn Gln Val Leu Ser Val Arg Ile Ala
                100                 105                110

Asp Lys Lys Tyr Tyr Pro Ser Ser Gln Asp Ser Ser Ser Ala Ala Ala
                115                 120                125

Pro Gln Leu Leu Ile Val Leu Leu Gly Leu Ser Ala Leu Leu Gln
        130                 135                140

<210> SEQ ID NO 19
<211> LENGTH: 126
<212> TYPE: PRT
<213> ORGANISM: Artificial Sequence
<220> FEATURE:
<223> OTHER INFORMATION: Description of Artificial Sequence: Synthetic
      amino acid sequence of a fusion protein
      comprising HA peptide and C-terminal lacking
      soluble HM 1.24 antigenic protein

<400> SEQUENCE: 19

Tyr Pro Tyr Asp Val Pro Asp Tyr Ala Gly Thr Asn Ser Glu Ala Cys
1               5                   10                 15

Arg Asp Gly Leu Arg Ala Val Met Glu Cys Arg Asn Val Thr His Leu
                20                  25                 30

Leu Gln Gln Glu Leu Thr Glu Ala Gln Lys Gly Phe Gln Asp Val Glu
                35                  40                 45

Ala Gln Ala Ala Thr Cys Asn His Thr Val Met Ala Leu Met Ala Ser
        50                  55                 60

Leu Asp Ala Glu Lys Ala Gln Gly Gln Lys Lys Val Glu Glu Leu Glu
65                  70                  75                 80

Gly Glu Ile Thr Thr Leu Asn His Lys Leu Gln Asp Ala Ser Ala Glu
                85                  90                 95

Val Glu Arg Leu Arg Arg Glu Asn Gln Val Leu Ser Val Arg Ile Ala
                100                 105                110

Asp Lys Lys Tyr Tyr Pro Ser Ser Gln Asp Ser Ser Ser Ala
                115                 120                125

<210> SEQ ID NO 20
<211> LENGTH: 126
<212> TYPE: PRT
<213> ORGANISM: Artificial Sequence
<220> FEATURE:
<223> OTHER INFORMATION: Description of Artificial Sequence: Synthetic
      amino acid sequence of L chain V region
      version a of humanized anti-HM 1.24 antibody

<400> SEQUENCE: 20

Met Gly Trp Ser Cys Ile Ile Leu Ser Leu Val Ala Thr Ala Thr Gly
            -15                 -10                 -5

Val His Ser Asp Ile Gln Met Thr Gln Ser Pro Ser Ser Leu Ser Ala
-1  1               5                   10
```

```
Ser Val Gly Asp Arg Val Thr Ile Thr Cys Lys Ala Ser Gln Asp Val
        15                  20                  25

Asn Thr Ala Val Ala Trp Tyr Gln Gln Lys Pro Gly Lys Ala Pro Lys
        30                  35                  40                  45

Leu Leu Ile Tyr Ser Ala Ser Asn Arg Tyr Thr Gly Val Pro Ser Arg
                50                  55                  60

Phe Ser Gly Ser Gly Ser Gly Thr Asp Phe Thr Phe Thr Ile Ser Ser
                65                  70                  75

Leu Gln Pro Glu Asp Ile Ala Thr Tyr Tyr Cys Gln Gln His Tyr Ser
            80                  85                  90

Thr Pro Phe Thr Phe Gly Gln Gly Thr Lys Val Glu Ile Lys
        95                  100                 105
```

<210> SEQ ID NO 21
<211> LENGTH: 139
<212> TYPE: PRT
<213> ORGANISM: Artificial Sequence
<220> FEATURE:
<223> OTHER INFORMATION: Description of Artificial Sequence: Synthetic
      amino acid sequence coding of H chain V region
      version r of humanized anti-HM 1.24 antibody

<400> SEQUENCE: 21

```
Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
        30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Met Thr Ala Asp Lys Ser Thr Ser
                65                  70                  75

Thr Ala Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110                 115                 120
```

<210> SEQ ID NO 22
<211> LENGTH: 139
<212> TYPE: PRT
<213> ORGANISM: Artificial Sequence
<220> FEATURE:
<223> OTHER INFORMATION: Description of Artificial Sequence: Synthetic
      amino acid sequence of H chain V region
      version s of humanized anti-HM 1.24 antibody

<400> SEQUENCE: 22

```
Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
```

```
                30                  35                  40                  45
Glu Trp Met Gly Ser Ile Phe Pro Gly Asp Gly Asp Thr Arg Tyr Ser
                    50                  55                  60

Gln Lys Phe Lys Gly Arg Val Thr Ile Thr Ala Asp Lys Ser Thr Ser
                65                  70                  75

Thr Ala Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110             115                 120

<210> SEQ ID NO 23
<211> LENGTH: 180
<212> TYPE: PRT
<213> ORGANISM: Homo sapiens
<220> FEATURE:
<223> OTHER INFORMATION: Amino acid sequence of human HM 1.24
      antigenic protein expressed on cell membrane

<400> SEQUENCE: 23

Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
 65                 70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180
```

HM1.24—UTILIZING CANCER VACCINES

TECHNICAL FIELD

The present invention relates to a cancer vaccine utilizing a cancer antigen HM1.24, more particularly a cancer vaccine utilizing a dendritic cell which has been pulsed by an HM1.24 or into which an HM1.24-encoding gene has been transduced.

BACKGROUND ART

An HM1.24 is a type II transmembrane glycoprotein identified as a myeloma-specific antigen, and is expected to be a target molecule in the immunotherapy of multiple myeloma as well as other cancers where the tumour cells express HM1.24 antigen. In order to generate a protective anti-tumour response, an efficient presentation of an appropriate cancer antigen is required. A dendritic cell is one of the most efficient antigen-presenting cells, capable of priming a naive T cell, and inducing both a CD4 T helper cell response and a CD8 cytotoxic T cell response. Hence dendritic cells are ideal antigen-presenting cells for use in cancer immunotherapy. However, it has not become possible that a dendritic cell is employed as an antigen-presenting cell for an HM1.24 antigen to stimulate a T cell whereby generating a cytotoxic T cell and exerting damage on a cancer cell.

DISCLOSURE OF THE INVENTION

Accordingly, an objective of the invention is to provide a novel type cancer vaccine by generating cytotoxic T cells via utilization of dendritic cells as antigen-presenting cells for the HM1.24 antigen. The invention also provides a cancer vaccine containing as an active ingredient an HM1.24 protein or peptide itself. Furthermore, the invention provides a cancer vaccine containing as an active ingredient a DNA or an RNA encoding an HM1.24 protein or peptide.

Thus, the invention provides a cancer vaccine containing as an active ingredient the dendritic cell which has been pulsed by HM1.24 antigen, or into which an HM1.24-encoding gene has been transduced. Such an HM1.24 antigen may be an HM1.24 protein or an HM1.24 peptide, preferably a soluble HM1.24 peptide.

The invention also provides a cancer vaccine containing as an active ingredient an HM1.24 protein or an HM1.24 peptide. This HM1.24 peptide is preferably a soluble HM1.24 peptide.

The invention also provides a cancer vaccine containing as an active ingredient an HM1.24-encoding DNA or RNA. This DNA is preferably a cDNA.

BRIEF DESCRIPTION OF THE DRAWINGS

FIG. 4 shows cytotoxic activity of CTL generated against HM1.24. It shows background cell death of the autologous tumour cells, or plasma cells (PC) and allogeneic PC.

FIG. 6 shows cytotoxic activity of control CTL. It shows background cell death of the autologous PC and allogeneic PC.

FIG. 7 shows cytotoxic activity of control CTL. It shows killing by control CTL of the autologous PC and allogeneic PC.

FIG. 8 shows that cytotoxic activity of CTL generated against HM1.24, against autologous plasma cells is blocked by an anti-Class I antibody.

FIG. 14 shows CTL assay on patient 05, showing MHC Class I dependence, target specificity and HM1.24 specificity.

BEST MODE FOR CARRYING OUT THE INVENTION

Figure 1:
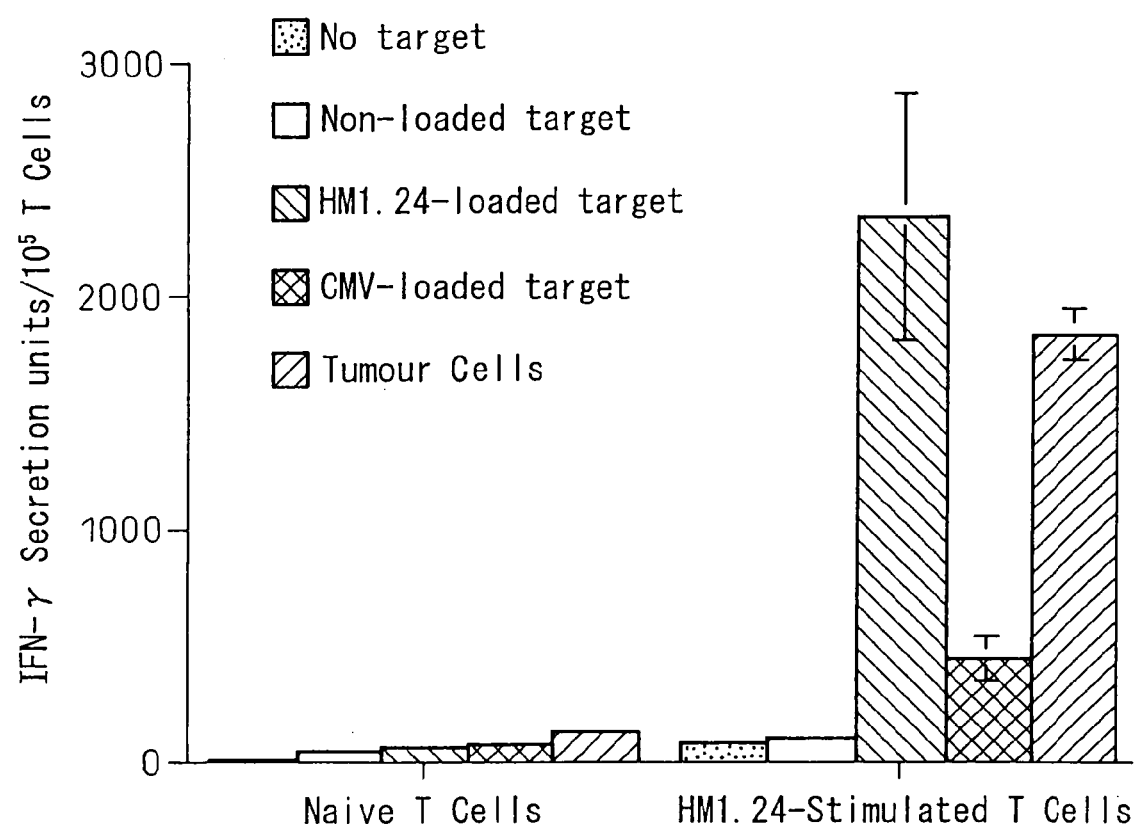
FIG. 1 is a graph showing the levels of the interferon-gamma production by T cells stimulated by dendritic cells pulsed with HM1.24 protein or non-stimulated naive T cells when such T cells were incubated in the presence of an HM1.24-loaded peripheral blood mononuclear cells (target cell), autologous tumour cells or other control cells.

The invention relates to a cancer vaccine containing as an active ingredient an antigen-specific dendritic cell which has been pulsed by an HM1.24 antigen, or into which an HM1.24-encoding gene has been transduced.

In an experimental animal, a higher immune response can be obtained by administering a dendritic cell into which an antigenic peptide or gene has been introduced rather than by administering the peptide or gene directly. As a method for expressing a high level of a cancer antigen in a dendritic cell, in vitro loading by a peptide or protein or DNA or RNA transduction is carried out. An immature dendritic cell is employed for the incorporation of a protein or an RNA that requires antigen processing, while a mature or dendritic cell activated for example by a CD40-ligand is employed for loading the peptide.

While an RNA or DNA can be transfected at a low rate into a dendritic cell, efficient transduction requires the use of a viral vector. It is also possible to use a method in which a cancer antigen is transduced into a CD34+ cell using a viral vector whereby effecting the differentiation into a cancer antigen-expressing dendritic cell after incubation in the presence of a GM-SF or a TNF-α.

A Dendritic cells are generally a cell population having a dendritic process serving as an auxiliary cell upon initiation of an immune response, which is derived from a bone marrow and in a close relationship with a macrophage, but has no phagocytic ability, and is distributed widely over the interstice of many organs, especially in a lymph node or spleen T cell region, and serves as an antigen-presenting cell for a helper T cell. The dendritic cell, in the context of the present invention, is considered to be involved in stimulating the differentiation of naive T cells into cytotoxic T cells when being pulsed by an HM1.24 protein or peptide. A similar effect is obtained also when an HM1.24-encoding gene has been transduced into a dendritic cell.

A dendritic cell employed for producing an inventive cancer vaccine is separated directly from peripheral blood by specific gravity centrifugation or derived from a precursor cell for example by cytokines. In a direct separation by the specific gravity centrifugation, a peripheral blood is subjected to an apheresis, from which a dendritic cell is separated by the specific gravity centrifugation and prepared. This method requires no cytokines and is less time-consuming. In this case, a mature dendritic cell is obtained and the degree of the maturity cannot be controlled. When being derived by a cytokine, a precursor cell may for example be a peripheral blood mononuclear cell adhesive cell fraction, a peripheral blood monocyte, i.e., CD14+ cell, or a myeloid or peripheral hematopoietic precursor cell, i.e., CD34+ cell.

As used herein, the expression that a dendritic cell is "pulsed" by an HM1.24 means that the HM1.24 protein or peptide is brought, alone or in combination with a pharmaceutically acceptable carrier such as a liposome, into contact with the dendritic cell over a predetermined period under a predetermined condition, and the time period of the contact may for example be several minutes to several days, and the condition and the method of the contact may be in accordance for example with those described in Chirava-Internati, M. et al., Blood (2002) 100, p. 961 to 965 (proteins), Thuner, B. et al., J. Exp. Med. (1999), 190, p. 1669-1678 (peptides).

In the invention, a method for transducing an HM1.24-encoding gene into a dendritic cell can be accomplished by transducing a DNA (preferably cDNA) or RNA directly or via the insertion into a suitable vector, preferably an expression vector capable of functioning in a mammal, especially in human. For example, a method described in Chiriva-Internati, M. et al., Blood (2002), 100, p. 961-965 can be employed.

A cancer vaccine containing as an active ingredient an antigen-specific dendritic cell which has been pulsed by an HM1.24 antigen, or into which an HM1.24-encoding gene has been transduced can be administered for example by a procedure in which a dendritic cell is collected from a patient, and this dendritic cell is pulsed with an HM1.24 protein or peptide as described above or transduced with an HM1.24-encoding gene as described above and subsequently this cell is introduced into the patient described above or other patients.

The invention further relates to a cancer vaccine containing as an active ingredient an HM1.24 protein or an HM1.24 peptide. When using an HM1.24 protein or an HM1.24 peptide as an immunogen, it is preferable to use a CD4+ T cell recognition antigen in addition to a CD8+ T cell antigen, and as such an antigen (helper epitope), a highly immunogenic exogenous antigen such as a KHL or tetanus toxoid is employed, as well as a helper epitope of a cancer antigen itself.

By administering an antigen protein (HM1.24 protein) in the form of a granule such as a cholesterol-polysaccharide complex or a bead, the incorporation for example into a dendritic cell is effected, whereby enabling CD8+ T cell induction via presentation of appropriate immunogenic peptide/s on MHC class I molecules. It may also be possible to induce potent CD8+ T cell activity by using a fusion protein with a bacterial heat shock protein with potent adjuvant activity.

This vaccine can contain, in addition to an HM1.24 protein or peptide as an active ingredient, a pharmaceutically acceptable carrier, such as an adjuvant, for example, a mineral gel such as aluminum hydroxide; a surfactant such as lysolecithin and Pluronic polyol; a polyanion; a peptide; or an oily emulsion. A liposome inclusion, or a polysaccharide, and/or other agglomerations to be incorporated into the vaccine may also be contemplated.

The invention also relates to a cancer vaccine containing as an active ingredient a gene encoding an HM1.24 protein or peptide. A recombinant virus containing a cancer antigen gene can induce a potent anti-tumour immune response in mice via an intracellular high level expression of the antigen. It is also possible to coexpress many CTL and helper epitopes, and can be used in a wide range of the patients regardless of the HLA type. Nevertheless, it causes a potent anti-viral immune response which leads to a difficulty in conducting a repetitive administration, because of which it is preferable to provide a large number of different viral vectors in the case requiring a frequent immunization such as a cancer. Fat-parasitic bacteria are useful as vectors for vaccines since they enable the loading of the antigens on both of MHC class I and class II.

A direct administration of a DNA has an established efficacy when employed as a prophylactic inoculation in animals which is regarded as a DNA immunization method. A non-methylated CpG sequence of a bacterial DNA such as a plasmid has an adjuvant activity capable of effecting a Th1 activation essential for tumour rejection via an IL-12 production. A method for immunizing with an antigen gene-carrying plasmid via an intramuscular injection or a gene gun has a low immunizing effect when given in a single administration, but it can be administered repetitively and is expected to be combined with other immunization methods. In order to increase the immune efficacy, a fusion protein obtained by binding an epitope to a leader sequence or by binding an epitope directly to an HLA molecule can be employed.

The gene is preferably a DNA or an RNA, and the DNA is preferably a cDNA, and it is inserted into a suitable vector, preferably an expression vector capable of functioning in a mammal, especially in human, and subsequently administered to an animal, thereby allowing a cancer immune response to be developed.

A cancer vaccine according to the invention is effective especially against a cancer of an organ or a tissue which expresses HM1.24 antigen, and useful against a hematopoietic tumour or a solid tumour. The hematopoietic tumour may for example be a leukemia, lymphoma, myeloma and the like, and said leukemia may for example be acute myelocytic leukemia, chronic myelocytic leukemia, acute lymphocytic leukemia, chronic lymphocytic leukemia and the like, while said lymphoma may for example be Hodgkin's disease, T cell non-Hodgkin's lymphoma, B cell non-Hodgkin's lymphoma and the like, and said myeloma may for example be multiple myeloma.

A solid tumour may for example be cervical cancer, small cell lung carcinoma, non-small cell lung carcinoma, esophageal cancer, breast cancer, stomach cancer, colon cancer, rectal cancer, lung cancer, biliary cancer, pancreatic cancer, ovarian cancer, uteral cervical cancer, uteral corporeal cancer, prostate cancer, kidney cancer, bladder cancer, skin cancer, brain tumour, malignant glioma, pediatric solid cancer, malignant bone tumour, and the like. Those which may also be mentioned are the metastasis or the metastatic focus of the solid cancers described above as well as cancerous pleurisy, cancerous peritonitis and cancerous meningitis associated with the solid cancers.

The HM1.24 employed in this invention is an HM1.24 protein, preferably a soluble HM1.24 protein or peptide. The soluble HM1.24 antigen protein of the invention may be any protein as long as it has the amino acid sequence consisting of the amino acids from Asn in the position 1 through Gln in the position 132 in the amino acid sequence represented by SEQ ID No.5 and has a biological activity of the soluble HM1.24 antigen protein. The biological activity of the soluble HM1.24 antigen protein means the property that the protein is bound specifically to an anti-HM1.24 antibody, is not bound to the cell membrane, is liberated from the cell membrane and thus soluble, and is a dimer.

An inventive soluble HM1.24 antigen protein may also be a soluble HM1.24 antigen protein which has the biological activity of a soluble HM1.24 antigen protein and has an amino acid sequence which has been modified by the substitution, deletion and/or addition of one or more amino acid residues in the amino acid sequence represented by SEQ ID No.5. More typically, the inventive soluble HM1.24 antigen protein may have an amino acid sequence undergoing the substitution of 1 or 2 or more, preferably 1 to 24, more preferably 1 to 12 amino acid residues in the amino acid sequence represented by SEQ ID NO.5, as long as it has the biological activity of the soluble HM1.24 antigen protein.

Alternatively, an amino acid sequence undergoing the deletion of 1 or 2 or more, preferably 1 to 42, more preferably 1 to 17 amino acid residues in the amino acid sequence represented by SEQ ID NO.5 may also be contemplated. Alternatively, an amino acid sequence undergoing the addition of 1 or 2 or more, preferably 1 to 50, more preferably 1 to 14 amino acid residues in the amino acid sequence represented by SEQ ID NO.5 may also be contemplated. A soluble HM1.24 antigen protein employed in the invention may be modified by the substitution, deletion and/or addition of the amino acids described above which occur all at once.

A soluble HM1.24 antigen protein was proven to exhibit its biological activity when it possesses the amino acid sequence from Asn in the position 1 through Arg in the position 90 in the amino acid sequence represented by SEQ ID No.5. Accordingly, the soluble HM1.24 antigen protein of the invention may be a soluble HM1.24 antigen protein having the amino acid sequence from Asn in the position 1 through Arg in the position 90 in the amino acid sequence represented by SEQ ID No.5, or the amino acid sequence which has been modified by the substitution, deletion and/or addition of one or more amino acids in the amino acid sequence from Asn in the position 1 through Arg in the position 90.

A soluble HM1.24 antigen protein may be a soluble HM1.24 antigen protein having the amino acids from Arg in the position 90 through Gln in the position 132 in the amino acid sequence represented by SEQ ID No.5 or an amino acid sequence which has been modified by the substitution, deletion and/or addition of one or more amino acid residues in this amino acid sequence, as long as it retains its biological activity.

A soluble HM1.24 antigen protein having an amino acid sequence which has been modified by the substitution, deletion and/or addition of one or more amino acid residues in the amino acid sequence represented by SEQ ID No.5 may for example be a soluble HM1.24 antigen protein having the amino acid sequence represented by SEQ ID No.7 or 17, 10 or 18, or, 11 or 19.

It is known that the biological activity of a certain amino acid is preserved in a protein which has been modified by the substitution, deletion and/or addition of one or more amino acid residues in said certain amino acid sequence (Mark, D. F. et al., Proc. Natl. Acad. Sci. USA (1984), 81, 5662-5666, Zoller, M. J. & Smith, M. Nucleic Acids Research (1982) 10, 6487-6500, Wang, A. et al., Science 224, 1431-1433, Dalbadie-McFarland, G. et al., Proc. Natl. Acad. Sci. USA (1982), 79, 6409-6413).

An inventive soluble HM1.24 antigen protein may vary in terms of the amino acid sequence, the molecular weight, the isoelectric point, the presence or absence of added saccharide chains or the positions of added saccharide chains if any, the structures of the saccharide chains, the phosphorylation state and/or the presence or absence of disulfide bonds, depending on the species from which it is derived, the host by which it is produced, and/or the purification method. Nevertheless, it may be a protein having any structure as long as it can be employed preferably in the invention. The species from which the protein is derived preferably is human.

A DNA encoding an inventive soluble HM1.24 antigen protein may for example be a base sequence from the base adenine on the position 1 through the base guanine on the position 396 in the base sequence represented by SEQ ID No.5. The DNA encoding an inventive soluble HM1.24 antigen protein may be a DNA derived from any origin as long as it is a DNA having the base sequence represented by SEQ ID No.5. Such a DNA may for example be a genomic DNA, cDNA, synthetic DNA and the like. It may also be a DNA obtained from a cDNA library or genomic library derived from various cells, tissues or organs or species other than human, which may be a commercially available DNA library. A vector employed in such a library may be any vector including a plasmid, bacteriophage, YAC vector, and the like.

A DNA encoding an inventive soluble HM1.24 antigen protein may also be a DNA capable of hybridizing with the base sequence represented by SEQ ID No.5 and also encoding a polypeptide having the biological activity of the soluble HM1.24 antigen protein. The condition under which the DNA encodes the soluble HM1.24 antigen protein may for example be a suitably stringent condition allowing the DNA to be hybridized.

Such a hybridization condition may for example be a condition of a low stringency. The condition of a low stringency may be a washing condition involving 42° C., 5×SSC, 0.1% sodium dodecyl sulfate and 50% formamide. More preferably, a condition of a high stringency may be mentioned. The condition of a high stringency may for example be a washing condition involving 60° C., 0.1×SSC and 0.1% sodium dodecyl sulfate. It is known that a protein encoded by a DNA capable of hybridizing under a suitable condition with a base sequence encoding a certain protein has the biological activity similar to that possessed by this certain protein.

Accordingly, an inventive soluble HM1.24 antigen protein includes a protein which is encoded by a "DNA capable of hybridizing" described above and which has the biological activity of the soluble HM1.24 antigen protein.

The amino acid sequence of a human HM1.24 antigen protein expressed on a cellular membrane is represented by SEQ ID No. 15 or 23. An *Escherichia coli* containing the plasmid pRS38-pUC19 having between the XbaI cleavage sites of a pUC vector a DNA encoding a human protein having the amino acid sequence represented by SEQ ID No.15 or 23 was designated as *Escherichia coli* DH5α (pRS38-pUC19), which was deposited internationally in compliance with the Budapest treaty under the deposition No. FERM BP-4434 dated Oct. 5, 1993, to National Institute of Bioscience and Human-Technology of Agency of Industrial Science and Technology (Higashi 1-1-3, Tsukuba, Ibaraki).

An inventive soluble HM1.24 antigen protein may also be a protein fused with other peptides or polypeptides as described above as long as it has the biological activity of the soluble HM1.24 antigen protein. The method for producing such a fusion protein may be any known method. Other peptides or polypeptides to be fused with the protein may be any peptide or polypeptide as long as it can be used effectively in the invention.

Such a peptide may for example be a known peptide such as FLAG (Hopp, T. P. et al., BioTechnology (1988), 6, 1204-1210), 6×His consisting of 6 His (histidine) residues, 10×His, Haemophilis influenza agglutinin (HA), human c-myc fragment, VSV-GP fragment, p18HIV fragment, T7-tag, HSV-tag, E-tag, SV40T antigen fragment, lck tag, a-tubulin fragment, B-tag, Protein C fragment, and the like.

As a polypeptide, those which can be exemplified are GST (glutathion-S transferase), HA, immunoglobulin constant region, β-galactosidase, MBP (maltose-binding protein), and the like. These may be any commercially available ones.

A DNA encoding an inventive protein can be constructed by using a DNA mentioned above together with a commercially available kit or a known method. For example, the construction may involve the digestion with a restriction enzyme, the addition of a linker, the insertion of an initiation codon (ATG) and/or a termination codon (ATT, TGA or TAG) and the like.

An expression vector of a protein of the invention may be any expression vector as long as it is an expression vector, which is employed preferably in the invention. Such an expression vector may for example be an expression vector derived from a mammalian animal, for example, pEF and PCDM8, an expression vector derived from an insect cell, for example pBacPAK8, an expression vector derived from a plant, for example, pMH1 and pMH2, an expression vector derived from an animal virus, for example, PHSV and pMV, an expression vector derived from an yeast for example, pNV11, an expression vector derived from *Bacillus subtilis*, for example, pPL603 and pKTH50, an expression vector derived from *Escherichia coli*, for example, PGEX, PGEMEX, pMALp2 and the like.

An inventive protein expression vector may be ligated for example with a soluble HM1.24 antigen protein-encoding DNA downstream of a promoter, which is then inserted into an expression vector, whereby accomplishing the production. The promoter/enhancer may for example be a promoter/enhancer derived from a mammalian animal, for example, EF1-α promoter/enhance, γ-actin promoter/enhancer, a promoter/enhancer derived from an insect virus, for example, cenocyte (polyhedrin) virus promoter/enhancer, a promoter/enhancer derived from a plant, for example tobacco mosaic virus promoter/enhancer, a promoter/enhancer derived from an animal virus, for example, SV40 promoter/enhancer and human CMV promoter/enhancer, a promoter/enhancer derived from a yeast, for example, alcohol dehydrogenase promoter/enhancer, a promoter/enhancer derived from *Escherichia coli*, for example, Lac promoter/enhancer, Trp promoter/enhancer, Tac promoter/enhancer, and the like.

The expression of an inventive protein may involve the addition of a signal sequence suitable for a host employed for the expression. Such a signal sequence may for example be a signal sequence of a secretory protein derived from a mammalian animal, for example, an immunoglobulin signal sequence. The secretory protein signal sequence may for example be a signal sequence of a secretory protein derived from *Escherichia coli*, for example, a periplasm secretory signal sequence such as OmpA.

An expression vector thus prepared may be transduced into a host by a known method. The transduction method may for a host by for example be an electroporation, calcium phosphate method, liposome method, and the like.

A protein employed in the invention can be obtained as a recombinant protein produced by a gene recombination technology described above. For example, the recombinant protein may produced in such a manner that the base sequence of a gene described here is cloned from a cell, tissue or organ expressing it and then integrated into a suitable vector, which is then transduced into a host cell where the production is effected. In the invention, such a recombinant protein can be employed.

Typically, from a cell, tissue or organ which expresses a protein employed in the invention, an mRNA encoding the respective gene is isolated. The isolation of the mRNA may be conducted by a known method such as a guanidine ultracentrifugation (Chirgwin, J. M. et al., Biochemistry (1979), 18, 5294-5299), an AGPC method (Chomozynski, P. and Sacch, N., Anal. Biochem. (1987), 162 (156-159), and the like to prepare a total RNA, from which the mRNA is prepared using an mRNA Purification Kit (Pharmacia) or equivalent. By using QuickPrep mRNA Purification Kit(Pharmacia), mRNA can be directly prepared.

The resultant mRNA is used together with a reverse transcriptase to synthesize a cDNA of the gene. The synthesis of the cDNA may be conducted also by using an AMV Reverse Transcriptase First-strand cDNA synthesis Kit (SEIKAGAKU KOGYO) or equivalent. It is also possible for synthesizing and amplifying a cDNA to employ a Marathon cDNA Amplification kit (CLONTECH) and a 5'-RACE method involving a polymerase chain reaction (PCR) (Frohman, M. A. et al., Proc. Natl. Acad. Sci. USA (1988)85, 8998-9002; Belyavsky, A. et al., Nucleic Acid Res. (1989)17, 2919-2932).

The resultant PCR is used to prepare an intended DNA fragment, which is then ligated with a vector DNA. Then this is used to prepare a recombinant vector, which is transduced for example into an *Escherichia coli* cell, the colonies of which are then selected to prepare a desired recombinant vector. The base sequence of the intended DNA is verified by a known method such as a dideoxynucleotide chain termination method. When the intended DNA is obtained, it is then integrated into an expression vector. More typically, a DNA constructed as described above can be expressed as described below, whereby obtaining the protein.

When a mammalian cell is employed, a customary useful promoter/enhancer, a gene to be expressed and a DNA having a poly-A signal bound 3'-downstream thereof in a functional manner or a vector containing it are employed for the expression. For example, the promoter/enhancer may for example be a human cytomegalovirus immediate early promoter/enhancer.

Other promoter/enhancers which can be employed for expressing a protein may be a viral promoter/enhancer derived from a retrovirus, polyoma virus, adenovirus, adenoassociated virus, simian virus 40 (SV40), and the like, and a mammalian cell-derived promoter/enhancer such as a human elongation factor 1α (HEF1α).

For example, it is convenient to use the method by Mulligan et al. (Nature (1979), 277, 108) when using an SV40 promoter/enhancer and the method by Mizushima et al. (Nucleic Acids Res. (1990), 18, 5322) when using an HEF1α promoter/enhancer.

When using an *Escherichia coli* cell, the expression can be conducted using a customary useful promoter, a signal sequence for the secretion of the protein and the gene to be expressed which are bound in a functional manner. The promoter may for example be lacZ promoter, araB promoter and the like. The lacZ promoter may be used in accordance with the method by Ward et al. (Nature, (1098), 341, 544-546;

FASEB J. (1992)6, 2422-2427), while the araB promoter may be used in accordance with the method by Better et al. (Science (1988) 240, 1041-1043).

A signal sequence for the protein secretion may be a pelB signal sequence (Lei, S. P. et al., J. Bacteriol. (1987)169, 4379) when the production is conducted by the periplasm of an *Escherichia coli* cell.

The replication origin may be one derived from Sv40, polyoma virus, adenovirus, bovine papilloma virus (BPV), and the like. For the purpose of increasing the number of the gene copies in a host cell line, the expression vector may contain, as a selection marker, an aminoglycoside phosphotransferase (APH) gene, a thymidine kinase (TK) gene, an *Escherichia coli* xanthine guanine phosphoribosyl transferase (Ecogpt) gene, a dihydrofolic acid reductase (dhfr) gene, and the like.

In the invention, any production system can be employed for producing a protein. The production system for producing the protein may be in vitro and in vivo production systems. As an in vitro production system, a production system using a eukaryote or a production system using a prokaryote.

When using a eukaryote, the production systems employing an animal cell, plant cell, and fungal cell are contemplated. The animal cell may be (1) a mammalian cell, for example, CHO (J. Exp. Med. (1995) 108, 945), COS, myeloma, BHK (baby hamster kidney) Hela, Vero, (2) an amphibious cell, for example, *Xenopus laevis* oocyte (Valle, et al., Nature (1981) 291, 358-340), or (3) an insect cell, for example, sf9, sf21 and Tn5. The CHO cell may preferably be a dhfr-CHO, which is a CHO cell having a DHFR gene defect (Proc. Natl. Acad. Sci. USA (1980) 77, 4216-4220) as well as a CHO K-1 (Proc. Natl. Acad. Sci. USA (1968) 60, 1275).

A plant cell may be a cell derived from *Nicotiana tabacum*, which may be subjected to a callus culture. A fungal cell may be an yeast such as *Saccharomyces* genus, including *Saccharomyces cerevisiae*, mold such as *Aspergillus* genus including *Aspergillus niger*.

When a prokaryote is employed, a production system employing a bacterial cell may be contemplated. The bacterial cell may be the cells of *Escherichia coli* and *Bacillus subtilis*.

Any of the cells listed above are transformed by an intended DNA, and the transformant is subjected to an in vitro culture, whereby obtaining the peptide. The culture may be in accordance with a known method. For example, a serum supplement such as a fetal calf serum (FCS) may be employed in combination, and a serum-free culture may also be mentioned. The pH during the culture is preferably about 6 to 8. The culture is conducted usually at 30 to 40° C. for about 15 to 200 hours, if necessary with exchange of the medium, aeration, and stirring.

On the other hand, an in vivo production system may for example be a production system using an animal or a production system using a plant. Such an animal or plant is transduced with an intended DNA, and the protein is produced in the body of the animal or plant and subsequently recovered.

When using an animal, production systems employing a mammalian animal and an insect are contemplated.

The mammalian animal may be a goat, pig, sheep, mouse and cattle (Vicki Glaser, SPECTRUM Biotechnology Applications, 1993). When using a mammalian animal, a transgenic animal can be employed.

For example, an intended DNA is inserted into the intermediate position of a gene encoding a protein produced specifically in a milk such as a goat β casein, whereby preparing a fusion gene. A DNA fragment containing this fusion gene into which the DNA has been inserted is injected into an embryo of the goat, and this embryo is then introduced into a female goat. In order to increase the quantity of the milk containing the protein produced by a transgenic goat, a hormone may be employed in the transgenic goat as appropriate (Ebert, K. M. et al., Bio/Technology (1994) 12, 699-702).

As an insect, a silkworm may be mentioned. When using a silkworm, the silkworm is infected with a baculovirus to which an intended DNA has been inserted, and then a desired protein is obtained from the body fluid of this silkworm (Susumu, M. et al., Nature (1985)315, 592-594).

When using a plant, a tobacco plant may be mentioned. When using a tobacco plant, an intended DNA is inserted into a plant expression vector, such as pMON530, and this vector is transduced into a bacterial cell such as an *Agrobacterium tumefaciens* cell. With this bacterial cell, a *Nicotiana tabacum* plant, for example, is infected, and then a desired protein is obtained from the leaves of this tobacco plant (Julian, K.-C. Ma et al., Eur. J. Immunol. (1994) 24, 131-138).

The method for transducing an expression vector into a host may be any known method, such as a calcium phosphate method (virology (1973) 52, 456-467 or an electroporation method (EMBO J. (1982) 1, 841-845). Also in view of the codon use frequency of the host employed for the expression, a sequence giving a further higher expression efficiency can be designed (Grantham, R. et al., Nucleic Acids Research (1981) 9, r43-r74).

Into such an animal or plant, a gene is transduced as described above to allow a protein to be produced in the body of the animal or plant, and then recovered. A protein which has been expressed and produced as described above can be separated from the inside or outside of a cell or from a host, and then purified until uniform. The separation and the purification of a protein employed in the invention is not limited particularly, and may be any separation and purification method employed for ordinary proteins.

For example, a chromatography column as an example of an affinity chromatography, filtration, ultrafiltration, salting out, dialysis, SDS polyacrylamide gel electrophoresis, isoelectric focusing, and the like may appropriately be selected or combined to perform the separation and the purification of a protein (SHINSEIKAGAKU JIKKENKOZA (1990), TOKYO KAGAKU DOJIN).

The chromatography may for example be an affinity chromatography, ion exchange chromatography, hydrophobic chromatography, gel filtration, reverse phase chromatography, adsorption chromatography and the like (Strategies for Protein Purification and Characterization: A Laboratory Course Manual. Ed. Daniel R. Marchak et al., Cold Spring Harbor Laboratory Press, 1996). Any of these chromatographies may be conducted by a liquid chromatography such as HPLC and FPLC.

EXAMPLES

The invention is further described in the following Examples.

Example 1

Effectiveness of Stimulation of T Cells by Dendritic Cell Pulsed with HM1.24

A leucapheresis fraction containing $3 \times 10^8$ peripheral monocytes was incubated for 2 hours in an RPMI medium containing 10% FCS to effect cell adhesion, and non-adhering cells were removed, and the culture medium was exchanged with an X-vivo 20 medium containing 10% autoserum, GM-CSF and IL-4, whereby dendritic cells were established. The dendritic cell thus prepared was pulsed by adding HM1.24 protein, and then incubated with 300 ng/ml of a CD40-ligand as a maturing agent, whereby accomplishing the maturation. Then, the dendritic cells were collected, washed with HBSS, and resuspended in X-vivo medium containing 5% autoserum. Cells were then irradiated at the dose of 25Gy, cells were washed again, and resuspended at the density of $3\times10^5$ cells/ml.

On the other hand, the frozen cells described above were thawed, washed, counted and resuspended in the medium containing IL-7 (10 ng/ml) and IL-12 (10 pg/ml) at the density of $3\times10^6$ cells/ml, and a 1 mL aliquot was added to each well together with 1 mL of the dendritic cells suspension. By replacing half of the medium, fresh IL-7 was added to the culture. The T cells were collected, counted, resuspended in a fresh medium at the density of $3\times10^6$ cells/ml, and added to a new 24-well plate containing fresh cytokines.

Then, T cells were re-stimulated twice at the interval of 1 week using dendritic cells prepared as above. During the last 5 days of this culture, interleukin-2 (IL-2) and interleukin-15 (IL-15) were added.

At the end of the culture, T cells were collected and examined for their ability of responding to an HM1.24-expressing stimulator cell (peripheral blood mononuclear cells loaded with HM1.24 and irradiated, and autologous tumour cells or plasma cells (PC)) by means of an ELISpot assay. In this ELISpot assay, T cells, which secreted a cytokine (IFN-γ) (antigen-specific T cell) were enumerated by ELISA. T cells were also tested for responses to non-loaded autologous peripheral blood mononuclear cells as negative control stimulator cells. Control T cells raised against the cytomegalovirus (CMV) antigen, pp65 were employed as negative control responder cells.

The results are shown in Table 1.

TABLE 1

| Stimulator cell (target cell) | Number of INF-γ units per $10^5$ T cells (mean ± SE, n = 3) |
|---|---|
| None | 86 ± 11 |
| Non-loaded PBMC | 106 ± 6 |
| HM1.24-loaded PBMC | 2341 ± 523 |
| CMV-loaded PBMC | 442 ± 95 |
| Autologous tumour cell | 1836 ± 111 |

As evident from the table shown above, the T cell when challenged with the target loaded with the HM1.24 produced a high level of the cytokine (INF-γ), and this level was significantly higher when compared with the cytokine production response to the negative controls. The cytokine production in the presence of the control antigen CMV was extremely low, indicating that the T cell described above was specific to the HM1.24. It was rather interesting that the T cell described above reacted markedly with the autologous tumour cell expressing the HM1.24. The results shown in Table 1 are indicated in FIG. 1 in comparison with the results of the similar procedure using a freshly isolated (naive) T cell (T cell which was not subjected to the treatment described in the first paragraph of Example 1).

Figure 2:
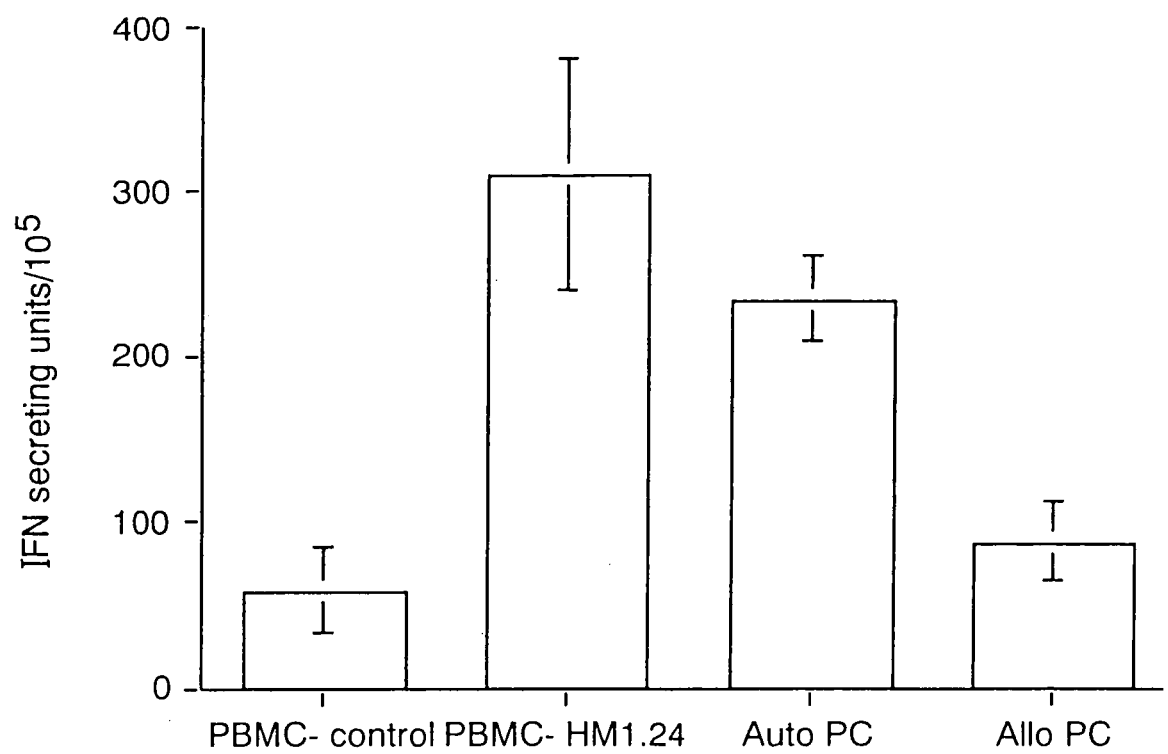
FIG. 2 is a graph showing the cumulative results of interferon-gamma production by T cells from 5 patients in an ELISpot assay. These T cells have been stimulated by dendritic cells pulsed with HM1.24 protein.

When tested in an ELISpot assay in 5 MM patients, HM1.24-specific T cells responded to HM1.24 loaded PBMC and also to autologous plasma cells but not to control PBMC, and only minimally to allogeneic tumour cells. The results are shown in FIG. 2.

Example 2

We proceeded to test the cytolytic capability of these HM1.24 specific T cells. Plasma cell targets were labeled with PKH26, incubated with effector T cells for 3 hours at 37° C., and TOPRO-3-iodide was added to stain the dead cells. Percent live/dead targets were then quantified by flow cytometry.

Baseline target cell death ranged from 4-24% with a median of 9.8%. T cells raised against HM1.24 demonstrated potent cytotoxic activity against autologous plasma cells (E:T ratio 20:1 median 63% specific killing, range 33-79%, E:T ratio 10:1 median 55%, range 21-75%, n=4) but not against allogeneic plasma cells (median 4% killing, range 0-9.7%).

Control T cells generated from co-culture with non-protein pulsed DC demonstrated minimal cytotoxicity against either autologous (median 13.7% killing range 11-20, n=3) or allogeneic (5.0%, 11.0% killing) plasma cells. CTL activity against autologous plasma cells was inhibited by anti-Class I mAb (median 94% inhibition, range 82-100%) but not by anti-Class II mAb (0% inhibition). CTL killing of autologous plasma cells was also blocked by prior incubation of T cells with Concanamycin A (87%, 91% inhibition) but not by pre-incubation with Brefeldin (0% inhibition).

Figure 3:
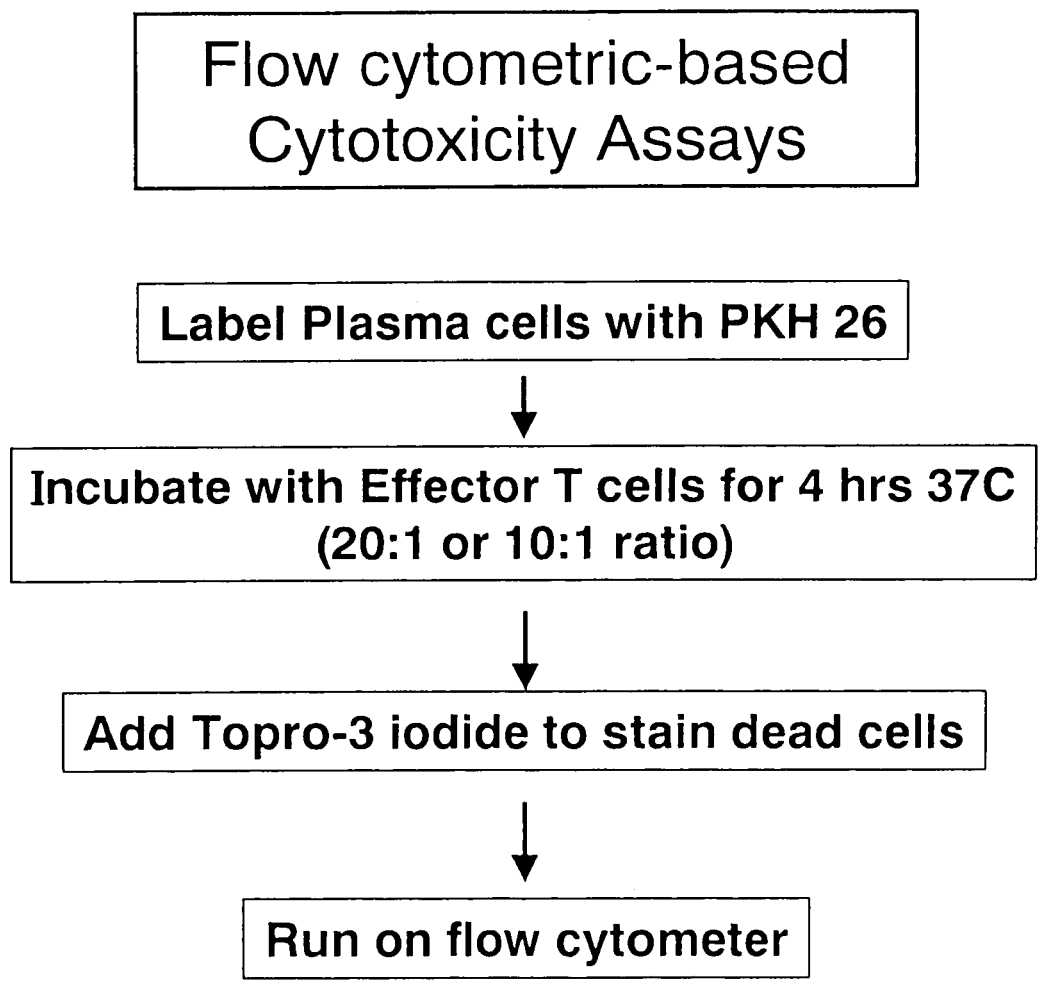
FIG. 3 shows a process for carrying out flow cytometric-based cytotoxicity assays.

Blocking Class I and II mAbs were used at 100 μg/mL.
Anti-Class I mAb: W6/32 clone, Serotec, UK
Anti-Class II mAb: B1.12 clone, Immunotech, France
Concanamycin A (used at 100 nM): Sigma Aldrich, UK
Brefeldin A (used at 10 μM): Sigma Aldrich, UK
Results are shown in FIGS. 3 to 11. FIG. 3 shows a process for carrying out flow cytometric-based cytotoxicity assays.

Figure 5:
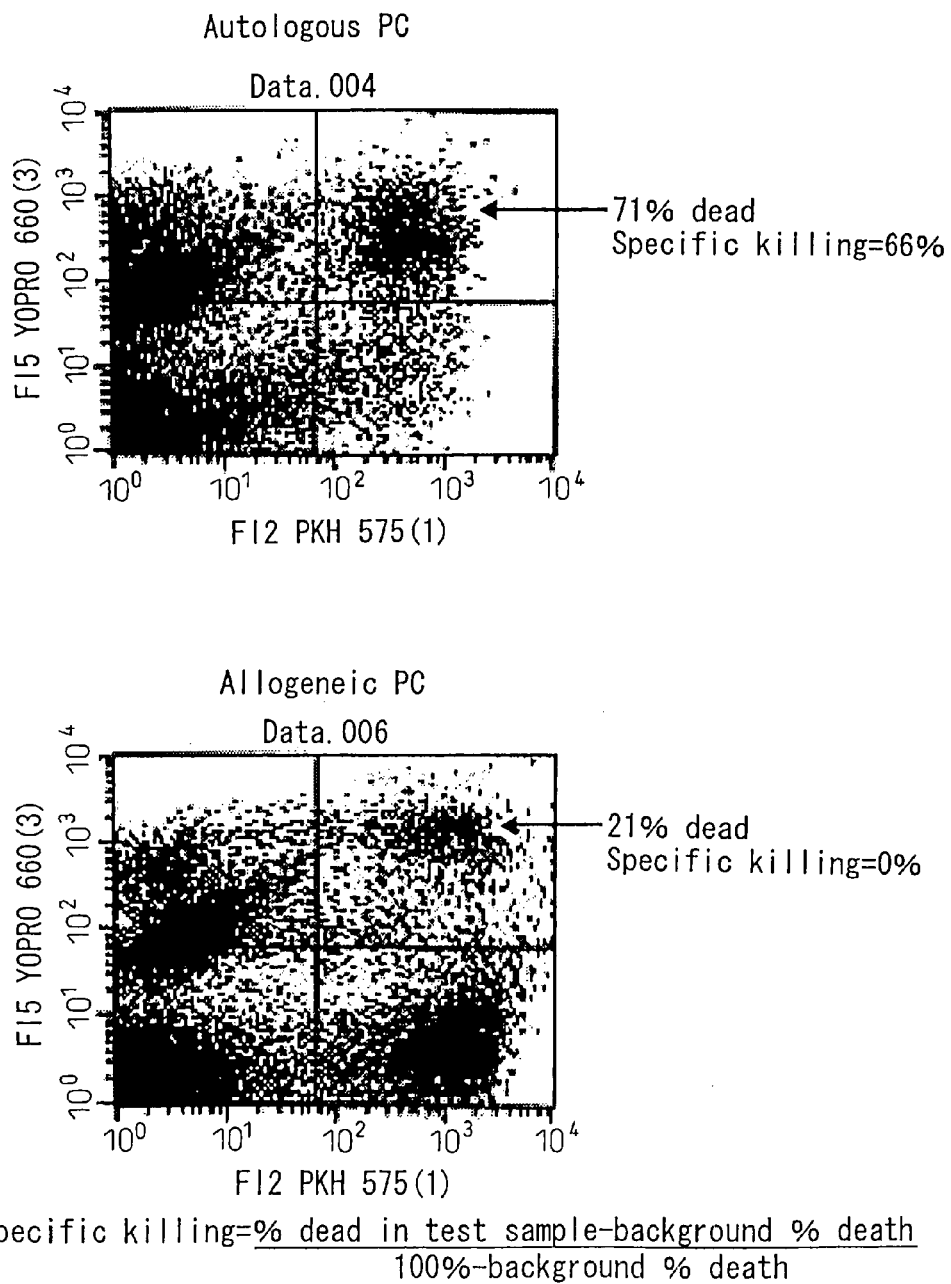
FIG. 5 shows cytotoxic activity of CTL generated against HM1.24. It shows specific killing by cytotoxic T lymphocytes (CTL) generated against HM1.24 of the autologous PC compared with allogeneic PC.

FIGS. 4 and 5 show cytotoxiic activity of CTL generated against HM1.24. FIG. 4 shows background cell death regarding the autologous PC and allogeneic PC. FIG. 5 shows specific killing by cytotoxic T lymphocytes (CTL) generated against HM1.24 regarding the autologous PC and allogeneic PC.

FIGS. 6 and 7 show cytotoxic activity of control CTL. FIG. 6 shows background cell death regarding the autologous PC and allogeneic PC. FIG. 7 shows killing by control CTL regarding the autologous PC and allogeneic PC.

FIG. 8 shows that cytotoxic activity of CTL against autologous plasma cells is blocked by an anti-Class I antibody. The killing of autologous plasma cells by HM1.24 CTL (E:T ratio 10:1) is blocked by pre-incubation of target cells with an anti-Class I antibody, but not affected by an antibody against Class II. The background cell death in the presence of an anti-Class I antibody was 13%, and that in the presence of an anti-Class II antibody was 20%.

Figure 9:
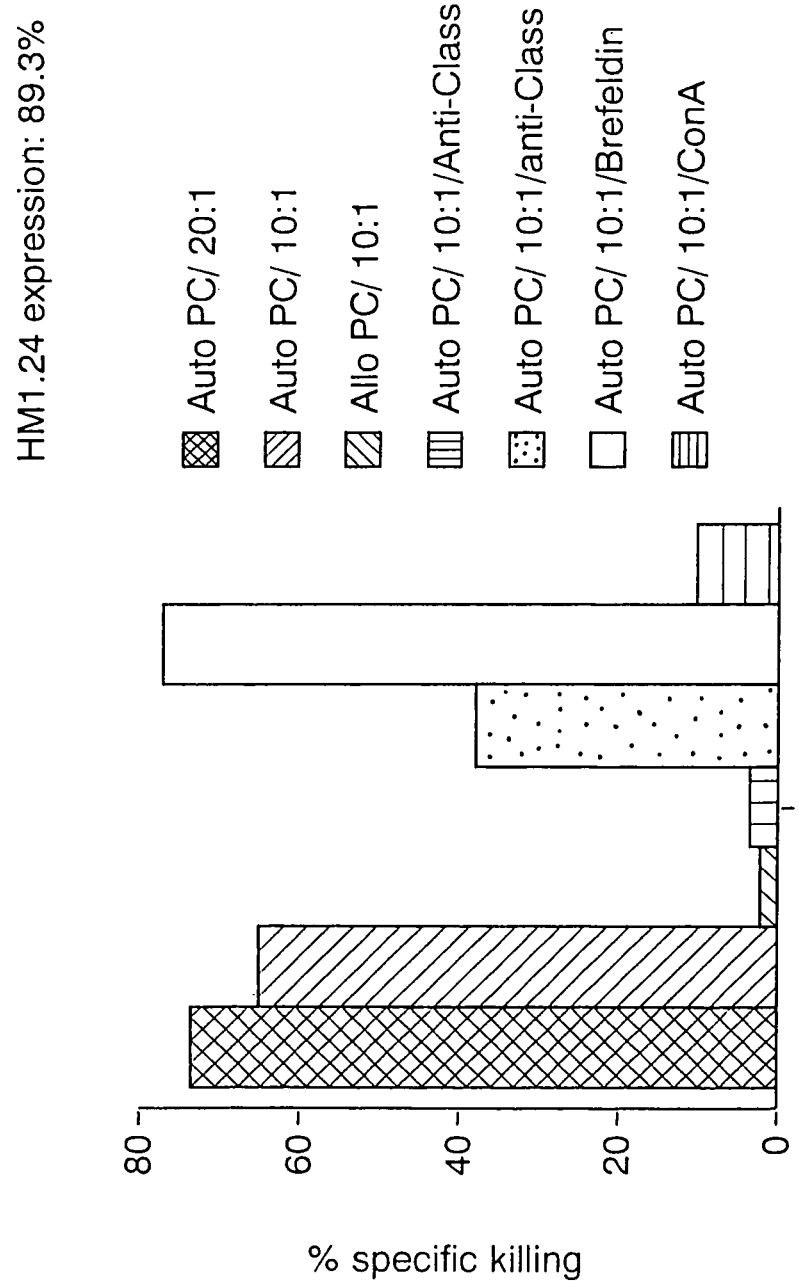
FIG. 9 shows cytotoxicity of CTL generated by co-culture and re-stimulation with HM1.24 loaded DC.

FIG. 9 shows cytotoxicity of CTL generated by co-culture and re-stimulation with HM1.24 loaded DC. Data are mean of duplicate determinations. Specific killing is calculated after subtracting baseline cell death. For MHC studies, anti-Class I or II mAbs were pre-incubated with targets for 30 minutes. For experiments to test the mode of cytotoxicity, CTL were pre-incubated with Brefeldin A, or Con A for 2 hours. The patient (Stage II IgG myeloma) was tested at the time of PBPC harvest, in PR after VAD chemotherapy. The patient (Stage II IgG myeloma) was tested at time of PBPC harvest, in PR after VAD.

Figure 10:
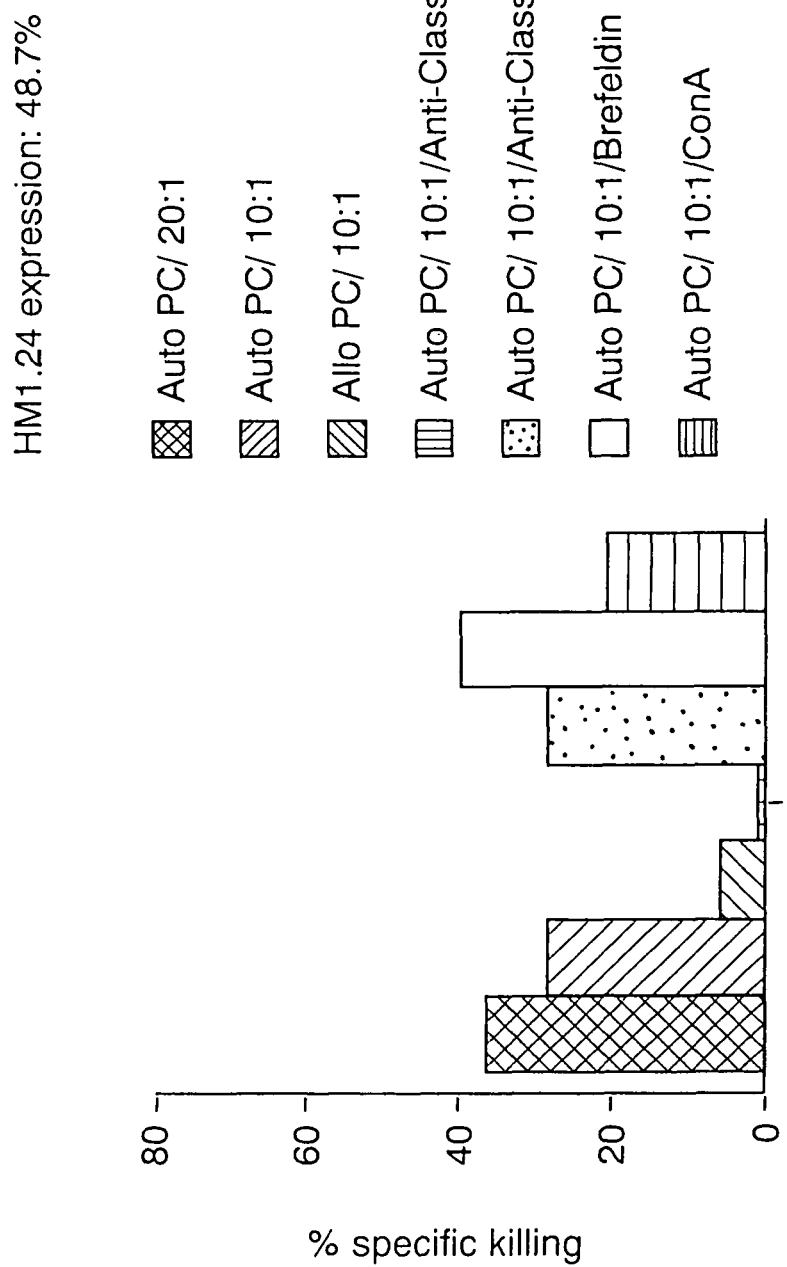
FIG. 10 shows CTL assay on T cells generated by co-culture and re-stimulation with HM1.24 loaded DC.

FIG. 10 shows CTL assay on T cells generated by co-culture and re-stimulation with HM1.24 loaded DC. Data and methods are the same as described for FIG. 9. The patient (Stage III Light Chain myeloma) was tested at the time of diagnosis, and MNCs used to generate DC were taken between courses of chemotherapy.

Figure 11:
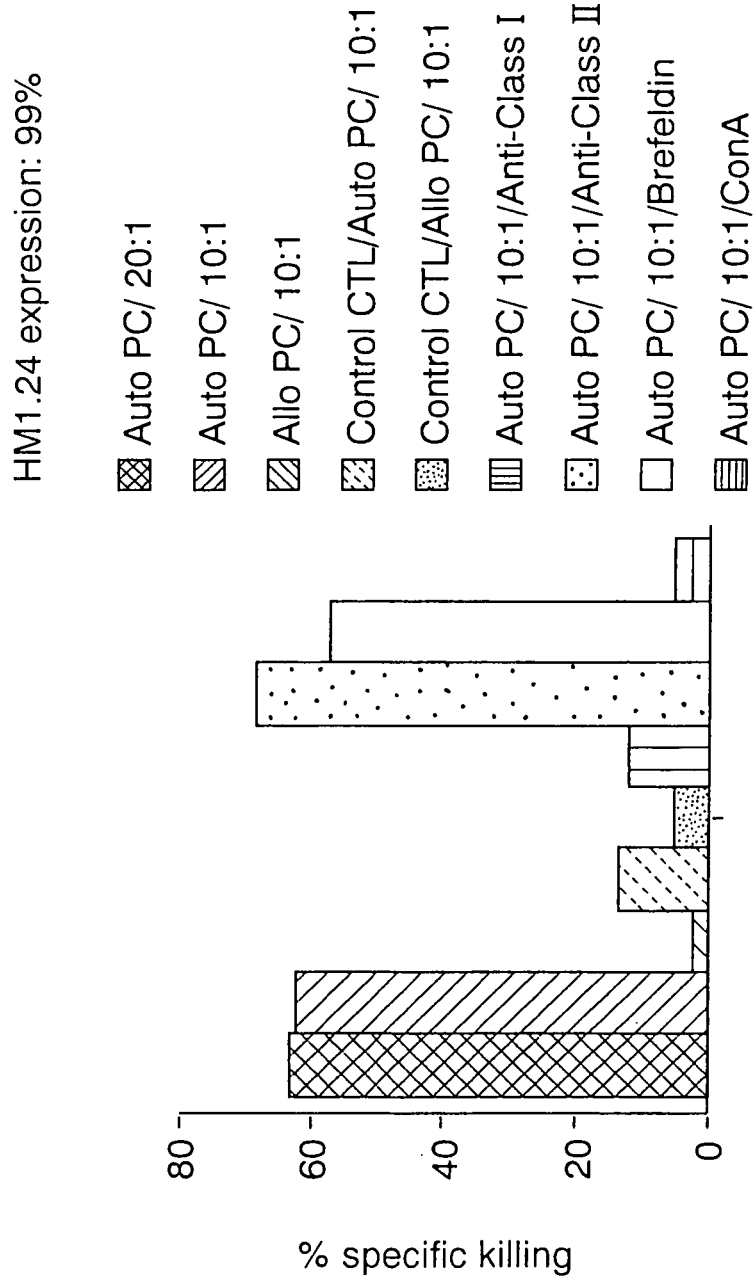
FIG. 11 shows CTL assay on Patient 03, showing target specificity, effector specificity, Class I dependence and blockade with Concanamycin A.

FIG. 11 shows CTL assay on Patient 03, showing target specificity, effector specificity, Class I dependence and blockade with Concanamycin A. Methods used are the same as described for FIG. 9. Control T cells are T cells harvested from co-cultures with non-protein loaded DC and serve as negative control CTL. All other results displayed refer to cytotoxicity of HM1.24 specific T cells. Data are as for FIGS. 9 and 10. The patient has Stage III IgG myeloma, chemoresistant. T cells were obtained prior to high dose melphalan.

Example 3

Finally, the lysis of autologous plasma cells by HM1.24 specific CTL was blocked in the presence of competitive "cold" targets, which were autologous DC transfected with cDNA encoding HM1.24 (43.8% inhibition when "cold" targets were present at a 3:1 ratio, 93.4% inhibition at a 10:1 ratio). Blocking of plasma cell lysis was not observed when unmanipulated DC were present in the cytotoxicity assay. HM1.24 primed T cells comprised 66±8% CD3+ CD8+T cells, with the remainder being CD3+ CD4+ cells.

Transfection of DC with Plasmid DNA Containing HM1.24

Plasmid DNA was isolated using Megaprep and quantified by spectrophotometry. The transfection mixture was made up using serum free medium (X-vivo 10, Life Technologies, UK) with FuGENE 6 transfection reagent (Roche Diagnostics Corporation, USA) and plasmid DNA. The FuGENE reagent was used at 6 µL to 2 µg of DNA, in a total volume of 100 µL, and the mixture was allowed to stand at room temperature for up to 2 hours before adding to DC in serum free medium. After 6 hours incubation, serum and fresh cytokines were added to the DC cultures. DC were analysed for expression of HM1.24 at 48 hours after transfection.

Ohtomo T. Biochem Biophys Res Commun. 1999 May 19; 258(3):583-91. Molecular cloning and characterization of a surface antigen preferentially overexpressed on multiple myeloma cells.

Figure 12:
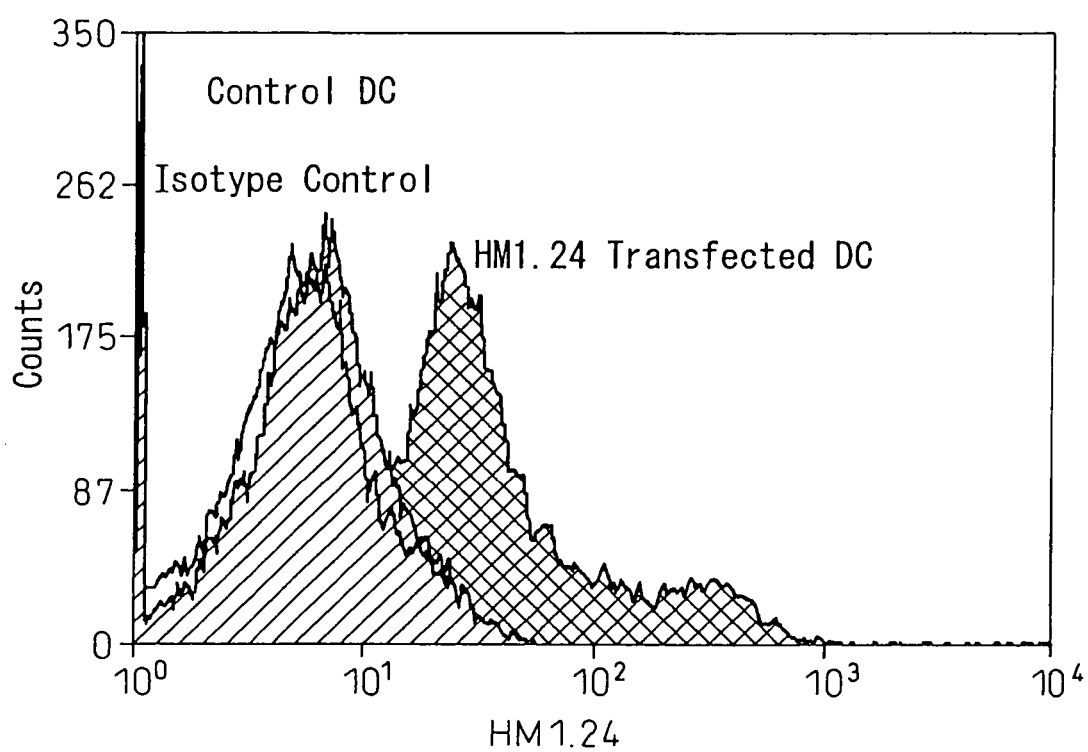
FIG. 12 shows that autologous DC transfected with HM1.24 plasmid express HM1.24 protein as detected by FACS assay.
Figure 13:
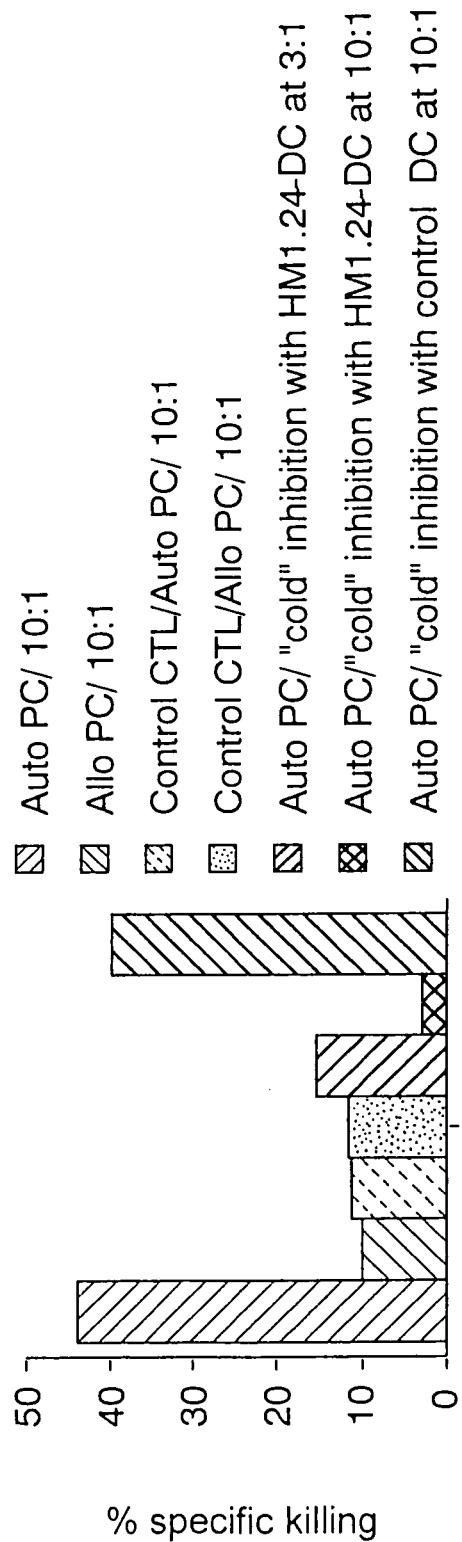
FIG. 13 shows CTL assay on patient 04, showing effector specificity, target specificity and that killing of autologous PC is blocked by the presence of HM1.24-expressing autologous DC which are acting as "cold" competitors.

Results are shown in FIGS. 12 to 14. FIG. 12 shows that autologous DC transfected with HM1.24 plasmid express high levels of HM1.24 antigen. The autologous DC transfected on day 4 with Fugene under serum free conditions were used on day 6 in the CTL assay at a 10:1 ratio with autologous plasma cells.

FIG. 13 shows the CTL assay on patient 04, showing effector specificity, target specificity, and HM1.24 specificity. Methods are as for FIGS. 9 to 12. Last 3 bars refer to experiments where autologous DC transected with cDNA encoding for HM1.24 (HM1.24-DC) are incubated in the CTL assay as "cold" competitor cells. Ratios of "cold" competitors to target PC are indicated. Control DC are unmanipulated autologous DC. The patient has IgG and IgA secreting myeloma and amyloidosis; patient is chemo-resistant, tested after failed AVD chemotherapy.

FIG. 14 shows the CTL assay on patient 05 showing MHC Class I dependence and HM1.24 specificity. Methods are as for FIGS. 9 to 13. "Cold" competitor cells were present at 10:1 ratio with autologous PC. Patients (Stage III IgG myeloma) were tested at diagnosis. T cells were obtained prior to treatment, DC for re-stimulation were obtained between courses of Melphalan.

Reference Example 1

Construction of Expression Plasmid for Soluble Human HM1.24 Antigen

An HEF expression vector (WO92-1975) containing EF1 α promoter which was prepared by means of the digestion by EcoRI (TAKARA) and NotI (TAKARA) and a gene pair encoding an Ig leader sequence and an HA tag (Amersham Pharmacia) were ligated by the reaction at 16° C. for 3 hours in a reaction mixture containing 50 mmol/L Tris-HCl, pH 7.6, 10 mM MgCl$_2$, 10 mmol/L dithiothreitol, 1 mmol/L ATP, 50 mg/ml polyethylene glycol and 10 units of T4 DNA ligase (TOYOBO).

The inserted leader sequence- and HA tag-encoding genes were the synthetic gene pair represented by SEQ ID NOS. 1 and 2 in which EcoRI, KpnI (TAKARA), and NotI restriction enzyme recognition sites were attached as linkers. Subsequently, the ligation reaction mixture was added to an E. coli DH5α competent cell (GIBCO-BRL) and the mixture was allowed to stand for 30 minutes on ice, 1 minute at 42° C., and 1 minute again on ice.

Then, 400 µl of an SOC medium (Molecular Cloning: A Laboratory Manual, Sambrook et al., Cold Spring Harbor Laboratory Press, (1989)) was added, and the mixture was incubated for 1 hour at 37° C., and then the E. coli was inoculated on an LB agar medium containing 50 µg/ml ampicillin (Molecular Cloning: A Laboratory Manual, Sambrook et al., Cold Spring Harbor Laboratory Press, (1989)), and incubated overnight at 37° C., thereby obtaining an E. coli transformant.

This E. coli transformant was cultured overnight at 37° C. in an LD medium containing 50 µg/ml ampicillin, and from this culture a plasmid DNA was prepared by an alkali method (Molecular Cloning: A Laboratory Manual, Sambrook et al., Cold Spring Harbor Laboratory Press, (1989)).

On the other hand, the HM1.24 antigen extracellular region gene was amplified by a PCR method using Thermal Cycler (Perkin Elmer Cetus). The cDNA of the HM1.24 antigen (SEQ ID No. 15) was used as a template and the mixture containing 100 pmol of the primers represented by SEQ ID Nos. 3 and 4, 10 mmol/L Tris-HCl, 50 mmol/L KCl, 0.1 mmol/L dNTPs (dATP, dGTP, dCTP, dTTP), 1.5 mmol/L MgCl$_2$ and 5 units of a DNA polymerase Ampli Taq (Perkin Elmer Cetus) was degenerated first at 94° C., subjected to 30 cycles each of which consisted of 1 minute at 94° C., 1 minute at 55° C., and 1 minute at 72° C., followed by final incubation for 10 minutes at 72° C.

The PCR product thus obtained was employed as an HM1.24 antigen extracellular region (SEQ ID No. 5) gene, which was ligated to the plasmid DNA described above which had been digested by KpnI and BamHI by the reaction for 3 hours at 16° C. in a reaction mixture containing 50 mmol/L Tris-HCl, pH 7.6, 10 mmol/L MgCl$_2$, 10 mM dithiothreitol and 1 unit of a T4 DNA ligase (TOYOBO). Similarly to the procedure described above, the ligation mixture was added to an E. coli DH5α competent cell to obtain an E. coli transformant, from which a plasmid DNA was prepared. The resultant plasmid DNA was designated as psHM which is an HA tag-carrying soluble antigen expression plasmid.

Using the primers represented by SEQ ID Nos. 3 and 6, an HM1.24 antigen extracellular region (SEQ ID No. 7)-expressing plasmid, namely, psHM164 in which the C terminal was also deleted was prepared similarly.

Nucleotide Sequence Determination

The bases of the psHM and the psHM164 were sequenced using an automatic DNA sequencer (Applied Biosystem Inc.) and a Taq Dye terminator Cycle Sequencing kit (Applied Biosystem Inc.) in accordance with the manufacturer's instruction protocol. The primers represented by SEQ ID Nos. 8 and 9 (Sawady Technology) were employed. As a result, the structure was revealed to allow a fusion protein of the soluble antigen ligated to the HA tag peptide (SEQ ID Nos. 10 and 11) to be expressed.

Reference Example 2

Establishment of Soluble Human HM1.24 Antigen High Expression Cell (1) Transfection of CHO Cell In order to establish an HA tag-carrying soluble HM1.24 antigen stable production system, the expression vectors described above which had been linearized by the digestion with PvuI (GIBO-BRL) (psHM and psHM164) were transduced into a CHO cell strain DXB11 (contributed by Medical Research Center) by means of an electroporation. 1 µg of the vector was added to a 0.8 ml aliquot of $1.1 \times 10^7$ cells/ml in PBS (−), and pulsed at 1.5 kV with the capacitance of 25 µF using a Gene Pulser device (Bio-Rad).

After the recovery period at room temperature for 10 minutes, the electroporated cell was suspended in 100 ml of an α-MEM (nucleoside-free) selection medium (GIBCO-BRL) containing 10% FCS (GIBCO-BRL) and 1% penicillin-streptomycin (GIBCO-BRL), and inoculated into a flat bottom 96-well plate in the volume of 100 µl/well ($1 \times 10^4$ cells/well). After culturing overnight in an incubator at 37° C. under 5% $CO^2$, 100 µl/well of the selection medium was further added to effect the selection. On the 14th day, the cell was assayed by a sandwich ELISA (see the section of strain selection) and 24 clones exhibiting a high expression of HA-sHM or HA-sHM164 were selected and propagated in a 24-well plate (1 ml/well). The clones selected in the nucleic acid-free medium were verified for their stable proliferation and then assayed again to select 10 clones each.

(2) Strain Selection

The soluble human HM1.24 ELISA described below was conducted as follows. In order to select a highly productive strain, the amount of the soluble protein produced was compared by a sandwich ELISA using anti-HA antibody (Boehringer Mannheim) and a humanized anti-HM1.24 antibody (K. Ono et al., The 20th Japan Molecular Biology Annual Meeting, General Lecture 3-501-P-478), whereby selecting the strain. Since the antigen concentration was not known because a purified antigen was not obtained, the number of the cells upon the ELISA was taken into account when comparing the concentration.

In this Example, as a reconstructed human anti-HM1.24 antibody (humanized anti-HM1.24 antibody), a light chain version a and a heavy chain version s described in WO98/14580 were employed. An *E. coli* cell having a plasmid containing the light chain version a was deposited internationally in compliance with the Budapest treaty under the deposition number FERM BP-5645 as *Escherichia coli* DH5α (pUC19-RVLa-AHM-gK) on Aug. 29, 1997 at the National Institute of Bioscience and Human-Technology of Agency of Industrial Science and Technology. On the other hand, an *E. coli* cell having a plasmid containing the heavy chain version s of the humanized anti-HM1.24 antibody was deposited internationally in compliance with the Budapest treaty under the deposition number FERM BP-6127 as *Escherichia coli* DH5α (pUC19-RVHs-AHM-gγ1) on Sep. 29, 1997 at the National Institute of Bioscience and Human-Technology of Agency of Industrial Science and Technology.

An anti-HA antibody (Boehringer Mannheim) was adjusted at 1 µg/ml in a Coating Buffer (C.B.: 0.1 mol/L sodium bicarbonate buffer, pH 9.6, 0.2% sodium azide) was added to a plane bottom 96-well plate (Nunc) in the volume of 100 µl/well, and coated overnight at 4° C.

To the anti-HA antibody coating plate washed three times with a PBS (−) containing 0.05% Tween 20 in the volume of 300 µl/well, 200 µl/well of a dilution buffer (50 mmol/L Tris-HCl, pH 8.1, 1 mmol/L $MgCl_2$, 0.15 mol/L NaCl, 0.05% Tween 20, 0.02% sodium azide, 1% BSA) was added and blocked for 2 hours at room temperature. After discarding the dilution buffer, 100 µl/well of the culture supernatant of a CHO cell as it was or diluted appropriately with the dilution buffer was added and reacted for 2 hours at room temperature.

As a positive control, a CGM/sHM (K. Ozaki et al., The 60th Japan Hematology Meeting, General Lecture 690) was employed. Then, 100 µl/well of a 1 µl/ml solution of a humanized anti-HM1.24 antibody (K. Ono et al., The 20th Japan Molecular Biology Annual Meeting, General Lecture 3-501-P-478) in the dilution buffer was added and reacted for 1 hour at room temperature. After washing similarly, 100 µl/well of a 5000-fold diluted alkaline phosphatase-labeled sheep anti-human IgG antibody (BIOSOURCE) in the dilution buffer was added, and reacted for 1 hour at room temperature.

Finally, the plate was washed five times, and received 100 µl/well of a 1 mg/ml solution of a SIGMA 104 (disodium p-nitrophenyl phosphate hexahydrate: SIGMA) in a substrate buffer (S.B.: 0.05 mol/L sodium bicarbonate buffer, pH 9.8, 10 mmol/L $MgCl_2$) to develop a color, and the absorbance at 405 nm to 655 nm was measured using a MICROPLATE READER (BIO-RAD).

A. Gene Amplification by 10 nmol/L MTX

Each of the 10 strains of DXB11 cells transduced with the expression vectors of a soluble HM1.24 antigen having the defect of the HM1.24 antigen transmembrane region (sHM) and sHM164 having the defect of the C terminal of the sHM each carrying an HA tag (sHM-producing strains: 1-1, 8-2, 9-3, 11-4, 14-5, -16, -17, 22, -23, -24, sHM164-producing strains: 164-1, -2, -3, -5, -6, -7, -8, -10, -13, -16) were cultured in 25 $cm^2$ flasks containing a 10 nmol/L methotrexate (MTX)-containing medium (α-MEM (GIBCO-BRL), 10% FCS (GIBCO-BRL, 1% penicillin-streptomycin (GIBCO-BRL), 100 nmol/L MTX (SIGMA)).

After 8 days, the antigen production level in the culture supernatant (3-day culture) was measured by ELISA. The sHM-producing strain 11-4 and the sHM164-producing strains 164-2 and 164-13 which exhibited a high expression level and a sufficient cell growth were subjected to gene amplification using 100 nmol/L MTX (see section B described below). The remainder of the strains was further cultured in a 10 nmol/L MTX medium since they had not been adapted to 10 nmol/L MTX yet.

After 11 days, the antigen production level in the culture supernatant (3-day culture) was measured by ELISA, and the sHM-producing strains 8-2, 9-3, 14-16 and 14-24 and the sHM164-producing strains 164-1, 164-5 and 164-8 which exhibited a high expression level were also subjected to gene amplification using 100 nmol/L MTX (see section B described below). The 164-13, which exhibited the highest production level at this time point exhibited the antigen production level about 10 times that of CGM/sHM (K. Ozaki et al., The 60th Japan Hematology Meeting, General Lecture 690).

B. Gene Amplification by 100 nmol/L MTX

Each of the 5 strains of the sHM-producing strains and the sHM164-producing strains which had exhibited high antigen production levels in the 10 nmol/L MTX medium (sHM-producing strains: 8-2, 9-3, 11-4, 14-16 and 14-24 and SHM164-producing strains: 164-1, 164-2, 164-5, 164-8 and 164-13) were subjected to gene amplification using 100 nmol/L MTX.

In the order of the adaptation to the 10 nmol/L MTX medium, the strains were subcultured into 25 $cm^2$ flasks in 1/15-, 1/10- or 1/5-volume depending on the number of the cells. After culturing for a day in the 10 nmol/L MTX medium, the medium was replaced with a 100 nmol/L MTX medium (α-MEM (GIBCO-BRL), 10% FCS (GIBCO-BRL), 1% penicillin-streptomycin (GIBCO-BRL), 100 nmol/L MTX (SIGMA)), and thereafter the culture was conducted in the 100 nmol/L MTX. The antigen production levels in the culture supernatant (2-day culture) of the sHM-producing strains 11-4 and the sHM164-producing strains 164-2 and 164-13 after 19 days and those of the sHM-producing strains 8-2, 9-3, 14-16 and 14-24 and the sHM164-producing strains 164-1, 164-5 and 164-8 after 8 days were measured by ELISA.

Each of the sHM-producing strain 8-2 and the sHM164-producing strains 164-2 and 164-13, which exhibited or were expected to exhibit a further high production level, continued to be cultured in the 100 nmol/L MTX medium, and examined again after 15 days for the antigen production level in the culture supernatant (3-day culture) by ELISA. Initially, the strain 164-2, which had exhibited the highest production, exhibited the antigen production level 5 times or more that of the CGM/sHM (K. Ozaki et al., The 60th Japan Hematology Meeting, General Lecture 690). After repetitive subcultures, however, the strain 164-2 which had exhibited the highest production exhibited the antigen production level slightly lower than that of CGM/sHM, showing the tendency of a reduction in the production level. Accordingly, it was decided to conduct a single cloning by a limiting dilution method.

C. Single Cloning by Limiting Dilution Method

The sHM-producing strain 8-2 and the sHM164-producing strains 164-2 and 164-13 were subjected to a single cloning by a limiting dilution method.

Each of the strains 8-2, 164-2 and 164-13 was adjusted at 1.7 cell/ml with the 100 nmol/L MTX medium, and dispensed in the volume of 150 μl/well (0.25 cells/well) into each of three 96-well plates. After culturing for 13 days, the culture supernatants (4-day culture) of the wells exhibiting the colony formation (8-2: 13 wells, 164-2: 36 wells, 164-13: 23 wells) were examined for the antigen production levels by ELISA.

From the wells exhibiting high production levels (8-2: 6 wells, 164-2: 15 wells, 164-13: 9 wells), the cells were subcultured into 24-well plates. Two plates, one for the subculture and the other for the measurement, were provided, and the medium in the plate for the measurement was replaced upon confluence, followed by culture for 3 days, after which the antigen production level in the culture supernatant was measured by ELISA.

From the strain 164-2 obtained from the 96-well plate, four strains (164-2-1, 164-2-13, 164-2-17 and 164-2-31) which exhibited the production levels about 100 times that from the CGM/sHM (K. Ozaki et al., The 60th Japan Hematology Meeting, General Lecture 690) were obtained finally.

D. Western Blotting

Each of the strains 164-2-1, 164-2-13, 164-2-17 and 164-2-31 was placed in 25 cm² flasks in 5 ml medium and the culture supernatant after 1, 3 or 5-day culture was subjected to a western blotting.

5 μl of the culture supernatant was made up to 10 μl in total using PBS(-), which was combined with an equal volume of an SDS-sample buffer solution (TEFCO, reduced). The mixture was heated at 100° C. for 5 minutes, and then an SDS-PAGE (18 mA, 1.5 hours) was performed. In this step, the gel employed was a mini-slab of 12.5% separation gel and 4.5% stack gel prepared by Laemi's method (Current Protocols in Molecular Biology 10.2.6-10.2.6). After running, the gel was transblotted (10 V, 30 minutes) onto a PVDF membrane (Millipore). The membrane was shaken in a 5% FBS-containing Tris buffer (TBS, TAKARA) at 25° C. for 1 hour, whereby effecting a blocking.

After rinsing with 0.05% Tween-containing TBS (TBS-T), a 50 μg/ml mouse anti-HM1.24 antibody (Blood (1994) 84, 1922-1930) was added, and the mixture was reacted with shaking at 25° C. for 2 hours. The buffer solution was exchanged 6 times at an interval of 10 minutes with shaking at room temperature while adding the TBS-T, whereby washing the membrane. Subsequently, a secondary antibody which was an alkaline phosphatase-labeled goat anti-mouse IgG (Zymed) after 2000-fold dilution with TBS-T was reacted similarly at 25° C. for 30 minutes with shaking.

After the reaction, TBS-T was added and the mixture was shaken at 25° C. for 10 minutes 6 times repetitively to wash the membrane. This membrane was subjected to color development using a BCIP/NBT color development substrate by immersing it in a western detection buffer (0.1 mol/L Tris-HCl buffer solution containing 0.1 mol/L NaCl, 5 mmol/L $MgCl_2$, pH 9.5) supplemented with 33 μL of nitroblue-tetrazolium (NBT) and 16.5 μL of 5-bromo-4-chloro-3-indolyl phosphate (BCIP).

After developing to an extent which caused no increase in the background, the membrane was washed with distilled water and the HM1.24 antigen was detected. All of the four clones (164-2-1, 164-2-13, 164-2-17, and 164-2-31) were in a reduced state, and the soluble antigen was detected as a broad band of 23-28 kDa which may reflect the heterogeniety due to the saccharide chain modification. Nevertheless, heterobands derived from the HM antigen protein were noted around 18 kDa and 14 kDa, and they were removed chromatographically to obtain the soluble antigen.

Reference Example 3

Purification of Soluble Human HM1.24 Antigen

From the culture supernatant of the soluble human HM1.24 antigen-expressing CHO cell, a soluble human HM1.24 antigen was purified. The soluble human HM1.24 antigen-expressing CHO cell was cultured at 37° C. in the presence of 5% $CO_2$ in a culture medium [α-MEM (GIBCO-BRL) containing 10% FBS (MOREGATE), 1% penicillin-streptomycin (GIBCO-BRL), and 500 nmol/L MTX (SIGMA)]. About 2 L of the culture supernatant was recovered by centrifugation.

A humanized anti-HM1.24 antibody conjugate affinity column (a CNBr-activated Sepharose 4FF conjugated with about 300 mg of the humanized anti-HM1.24 antibody) was loaded with the culture supernatant, washed with PBS (obtained by 10-fold dilution of 10XPBS; NACALAI) and then eluted with a 0.2 mol/L glycine buffer (pH 2.48). The resultant fraction was subjected to a reverse phase chromatography on a VyDac C4 column eluting with a gradient of acetonitrile to give a crude product.

The crude product was re-chromatographed twice using the similar reverse phase chromatography for the purification. The resultant purified product was subjected to a 5-fold dilution with PBS, and subjected to the buffer exchange to PBS using a Fast Desalting HR10/10 column. On the basis of the absorbance at 280 nm, the concentration of the resultant human HM1.24 antigen was calculated to be about 0.382 mg/ml, and 42 ml in total of the purified product was obtained. The purity on the basis of the area ratio of the reverse phase chromatography was 95% or higher.

INDUSTRIAL APPLICABILITY

As evident from the data shown above, T cells derived from patients with multiple myeloma responded in an antigen-specific manner to an HM1.24-expressing target cell after stimulation with HM1.24-expressing dendritic cells. These T cells demonstrated cytokine production and a cytotoxic response to HM1.24 expressing targets, including autologous tumour cells. Accordingly, a HM1.24 protein or peptide is immunogenic in a system based on the dendritic cell and capable of inducing a T cell-mediated response, and this response is antigen-specific and exerted toward the target cell.

Accordingly, a dendritic cell pulsed with an HM1.24 protein or peptide or transduced with an HM1.24-encoding gene, the HM1.24 protein or peptide itself, and an HM1.24 protein- or peptide-encoding DNA or RNA may be useful as a cancer vaccine.

The invention claimed is:

1. A cancer vaccine containing as an active ingredient a dendritic cell pulsed by a soluble HM1.24 protein, wherein the vaccine is used as a therapeutic and the soluble HM1.24 protein comprises the amino acid sequence shown in SEQ ID NO: 16 or SEQ ID NO: 17.

2. A cancer vaccine according to claim 1, wherein said cancer is a cancer of an organ or tissue which expresses an HM1.24 antigen.

3. A cancer vaccine according to claim 1, wherein the dendritic cell serves as an antigen-presenting cell for a helper T cell.

4. A cancer vaccine according to claim 1, wherein the vaccine is produced by a process comprising:
   (a) pulsing immature dendritic cells by the soluble HM1.24 protein, and
   (b) accomplishing the maturation.

5. A method for treating multiple myeloma in a patient, comprising administering to the patient the cancer vaccine according to claim 1, wherein the method comprises the steps of:
   (a) pulsing immature dendritic cells by a soluble HM1.24 protein comprising the amino acid sequence shown in SEQ ID NO: 16 or SEQ ID NO: 17;

(b) accomplishing the maturation of the dendritic cells; and
(c) administering the mature dendritic cells into the patient.

6. A method for generating T cells for treating multiple myeloma in a patient, comprising administering to the patient a dendritic cell pulsed by a soluble HM1.24 protein, wherein the soluble HM1.24 protein comprises the amino acid sequence shown in SEQ ID NO: 16 or SEQ ID NO: 17.

7. A method according to claim 6, wherein the method comprises the steps of:
  (a) pulsing immature dendritic cells by a soluble HM1.24 protein comprising the amino acid sequence shown in SEQ ID NO: 16 or SEQ ID NO: 17;
  (b) accomplishing the maturation of the dendritic cells; and
  (c) administering the mature dendritic cells into the patient.

8. A method according to claim 6, wherein the dendritic cell serves as an antigen-presenting cell for a helper T cell.

* * * * *

UNITED STATES PATENT AND TRADEMARK OFFICE
CERTIFICATE OF CORRECTION

PATENT NO. : 8,652,839 B2  
APPLICATION NO. : 10/533104  
DATED : February 18, 2014  
INVENTOR(S) : Kwee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this

Twenty-ninth Day of September, 2015

Michelle K. Lee  
*Director of the United States Patent and Trademark Office*